US009486692B2

(12) United States Patent
Crowley et al.

(10) Patent No.: US 9,486,692 B2
(45) Date of Patent: Nov. 8, 2016

(54) MONITORING OF PHYSICAL TRAINING EVENTS

(71) Applicant: InfoMotion Sports Technologies, Inc., Attleboro, MA (US)

(72) Inventors: Michael James Crowley, Attleboro, MA (US); Kevin King, Columbus, OH (US)

(73) Assignee: Russell Brands, LLC, Bowling Green, KY (US)

( * ) Notice: Subject to any disclaimer, the term of this patent is extended or adjusted under 35 U.S.C. 154(b) by 0 days.

(21) Appl. No.: 14/582,533

(22) Filed: Dec. 24, 2014

(65) Prior Publication Data

US 2015/0112464 A1 Apr. 23, 2015

Related U.S. Application Data

(63) Continuation of application No. 13/961,482, filed on Aug. 7, 2013, now Pat. No. 8,951,106, which is a continuation of application No. 13/259,842, filed as application No. PCT/US2010/029068 on Mar. 29, (Continued)

(51) Int. Cl.
*A63F 13/10* (2006.01)
*A63B 71/06* (2006.01)
(Continued)

(52) U.S. Cl.
CPC ........... *A63B 71/06* (2013.01); *A63B 24/0006* (2013.01); *A63B 24/0062* (2013.01); *A63B 43/00* (2013.01); *G06F 19/00* (2013.01); *G06F 19/3481* (2013.01); *A63B 24/0084* (2013.01); *A63B 69/002* (2013.01);
(Continued)

(58) Field of Classification Search
CPC ...................................................... A63F 13/10
See application file for complete search history.

(56) References Cited

U.S. PATENT DOCUMENTS 3,229,976 A   1/1966   Walter
4,479,649 A   10/1984  Newcomb et al.
(Continued)

FOREIGN PATENT DOCUMENTS

CN   1524004   8/2004
CN   1814333   8/2006
(Continued)

OTHER PUBLICATIONS

U.S. Appl. No. 61/028,823, filed Feb. 2008, Crowley.
(Continued)

*Primary Examiner* — Omkar Deodhar
(74) *Attorney, Agent, or Firm* — Bradley Arant Boult Cummings, LLP

(57) ABSTRACT

A computer-implemented method is disclosed that includes instructing a human player to perform a plurality of different actions in a determined order with a physical basketball, including actions of bouncing the physical basketball, and obtaining, with one or more electronic sensors, data that characterizes motion of the physical basketball being handled by the human player who is performing the instructed actions at a location. The method also includes communicating the data from the sensors to a console videogame system that is proximate to the location, and graphically representing, in a videogame displayed on a display device, performance by the human player, the performance being affected by the captured data, the representation of performance by the human player being compared against a standard of performance.

20 Claims, 28 Drawing Sheets

Related U.S. Application Data 2010, now Pat. No. 8,540,560.

(60) Provisional application No. 61/249,526, filed on Oct. 7, 2009, provisional application No. 61/164,277, filed on Mar. 27, 2009.

(51) Int. Cl.
| | |
|---|---|
| *A63B 24/00* | (2006.01) |
| *A63B 43/00* | (2006.01) |
| *G06F 19/00* | (2011.01) |
| *A63B 69/00* | (2006.01) |

(52) U.S. Cl.
CPC ... *A63B 69/0071* (2013.01); *A63B 2024/0012* (2013.01); *A63B 2024/0068* (2013.01); *A63B 2024/0096* (2013.01); *A63B 2071/0625* (2013.01); *A63B 2071/0655* (2013.01); *A63B 2220/22* (2013.01); *A63B 2220/35* (2013.01); *A63B 2220/40* (2013.01); *A63B 2220/51* (2013.01); *A63B 2220/53* (2013.01); *A63B 2220/56* (2013.01); *A63B 2220/803* (2013.01); *A63B 2220/833* (2013.01); *A63B 2225/20* (2013.01); *A63B 2225/50* (2013.01)

(56) References Cited

U.S. PATENT DOCUMENTS

| | | | |
|---|---|---|---|
| 4,577,865 | A | 3/1986 | Shishido |
| 4,595,200 | A | 6/1986 | Shishido |
| 4,776,589 | A | 10/1988 | Yang |
| 5,102,131 | A | 4/1992 | Remington |
| 5,236,383 | A | 8/1993 | Connelly |
| 5,609,411 | A | 3/1997 | Wang |
| 5,779,576 | A | 7/1998 | Smith et al. |
| 5,810,685 | A | 9/1998 | Willner et al. |
| 5,888,156 | A | 3/1999 | Cmiel et al. |
| 6,013,007 | A | 1/2000 | Root et al. |
| 6,148,271 | A | 11/2000 | Marinelli |
| 6,196,932 | B1 | 3/2001 | Marsh et al. |
| 6,251,035 | B1 | 6/2001 | Fa |
| 6,565,449 | B2 | 5/2003 | Buhler |
| 6,582,330 | B1 | 6/2003 | Rehkemper et al. |
| 6,671,390 | B1 | 12/2003 | Barbour et al. |
| 6,744,375 | B1 | 6/2004 | Groos |
| 6,757,572 | B1 | 6/2004 | Forest |
| 6,856,934 | B2 | 2/2005 | Vock et al. |
| 7,014,581 | B2 | 3/2006 | Ng |
| 7,021,140 | B2 | 4/2006 | Perkins |
| 7,072,789 | B2 | 7/2006 | Vock et al. |
| 7,092,846 | B2 | 8/2006 | Vock et al. |
| 7,162,392 | B2 | 1/2007 | Vock et al. |
| 7,192,387 | B2 | 3/2007 | Mendel |
| 7,234,351 | B2 | 6/2007 | Perkins |
| 7,273,431 | B2 | 9/2007 | DeVall |
| 7,308,818 | B2 | 12/2007 | Considine et al. |
| 7,625,314 | B2 | 12/2009 | Ungari et al. |
| 7,643,895 | B2 | 1/2010 | Gupta et al. |
| 7,813,822 | B1 | 10/2010 | Howell |
| 7,891,666 | B2 | 2/2011 | Kuenzler et al. |
| 8,070,654 | B2 | 12/2011 | Chapa, Jr. et al. |
| 8,078,478 | B2 | 12/2011 | Fleming et al. |
| 8,083,646 | B2 | 12/2011 | Chapa, Jr. et al. |
| 8,086,421 | B2 | 12/2011 | Case, Jr. et al. |
| 8,109,858 | B2 | 2/2012 | Redmann |
| 8,112,251 | B2 | 2/2012 | Case, Jr. et al. |
| 8,128,410 | B2 | 3/2012 | Prstojevich |
| 8,152,695 | B2 | 4/2012 | Riley et al. |
| 8,172,722 | B2 | 5/2012 | Molyneux et al. |
| 8,206,219 | B2 | 6/2012 | Shum et al. |
| 8,231,487 | B2 | 7/2012 | Nurnberg et al. |
| 8,231,506 | B2 | 7/2012 | Molyneux et al. |
| 8,517,870 | B2 | 8/2013 | Crowley et al. |
| 8,540,560 | B2 | 9/2013 | Crowley et al. |
| 8,579,632 | B2 | 11/2013 | Crowley |
| 8,597,095 | B2 | 12/2013 | Crowley et al. |
| 8,663,040 | B2 | 3/2014 | Kortegast |
| 8,951,106 | B2 | 2/2015 | Crowley et al. |
| 2003/0207718 | A1 | 11/2003 | Perlmutter |
| 2003/0224885 | A1 | 12/2003 | Leal et al. |
| 2003/0228934 | A1 | 12/2003 | Corzilius et al. |
| 2005/0069853 | A1 | 3/2005 | Tyson et al. |
| 2005/0288133 | A1 | 12/2005 | Rudell |
| 2006/0025282 | A1 | 2/2006 | Redmann |
| 2006/0135297 | A1 | 6/2006 | Cruciani |
| 2006/0148594 | A1 | 7/2006 | Saintoyant et al. |
| 2006/0166737 | A1 | 7/2006 | Bentley |
| 2006/0189386 | A1 | 8/2006 | Rosenberg |
| 2007/0021244 | A1 | 1/2007 | Ko |
| 2007/0026975 | A1 | 2/2007 | Marty et al. |
| 2007/0207873 | A1 | 9/2007 | Rose |
| 2007/0281811 | A1 | 12/2007 | Wang |
| 2008/0015064 | A1 | 1/2008 | Nelson et al. |
| 2008/0026877 | A1 | 1/2008 | Neel |
| 2008/0139307 | A1 | 6/2008 | Ueshima et al. |
| 2008/0269016 | A1 | 10/2008 | Ungari et al. |
| 2008/0300905 | A1 | 12/2008 | Kelley, III |
| 2009/0029754 | A1 | 1/2009 | Slocum et al. |
| 2009/0047645 | A1 | 2/2009 | Dibenedetto et al. |
| 2009/0048044 | A1 | 2/2009 | Oleson et al. |
| 2009/0048070 | A1 | 2/2009 | Vincent et al. |
| 2009/0112692 | A1 | 4/2009 | Steelberg et al. |
| 2009/0189982 | A1 | 7/2009 | Tawiah |
| 2009/0210078 | A1 | 8/2009 | Crowley |
| 2009/0298650 | A1 | 12/2009 | Kutliroff |
| 2009/0325739 | A1 | 12/2009 | Gold |
| 2010/0048302 | A1 | 2/2010 | Lutnick et al. |
| 2010/0053324 | A1 | 3/2010 | Kim et al. |
| 2010/0069181 | A1 | 3/2010 | Lin |
| 2010/0105480 | A1 | 4/2010 | Mikhailov et al. |
| 2010/0130315 | A1 | 5/2010 | Steidle |
| 2010/0184563 | A1 | 7/2010 | Molyneux et al. |
| 2010/0285903 | A1 | 11/2010 | Nicodem |
| 2011/0077112 | A1 | 3/2011 | Erario et al. |
| 2011/0118062 | A1 | 5/2011 | Krysiak et al. |
| 2011/0220634 | A1 | 9/2011 | Yeh |
| 2011/0316529 | A1 | 12/2011 | Stancil et al. |
| 2012/0029666 | A1 | 2/2012 | Crowley |
| 2012/0058845 | A1 | 3/2012 | Crowley |
| 2012/0129138 | A1 | 5/2012 | Redmann |
| 2012/0231906 | A1 | 9/2012 | Barry et al. |
| 2013/0079906 | A1 | 3/2013 | Crowley et al. |
| 2014/0031151 | A1 | 1/2014 | Crowley |
| 2014/0039651 | A1 | 2/2014 | Crowley |
| 2014/0081436 | A1 | 3/2014 | Crowley et al. |
| 2014/0106833 | A1 | 4/2014 | Mohn et al. |

FOREIGN PATENT DOCUMENTS

| | | |
|---|---|---|
| CN | 101367013 | 2/2009 |
| EP | 1 637 192 | 3/2006 |
| JP | 2007-014671 | 1/2007 |
| KR | 10-1988-0001317 | 4/1988 |
| KR | 2000055834 | 9/2000 |
| KR | 2001008367 | 2/2001 |
| WO | WO 95/34351 | 12/1995 |
| WO | WO 99/16511 | 4/1999 |
| WO | WO 03/022369 | 3/2003 |
| WO | WO 2009/102813 | 8/2009 |
| WO | WO 2012/033732 | 3/2012 |

OTHER PUBLICATIONS

U.S. Appl. No. 61/164,277, filed Mar. 2009, Crowley.
U.S. Appl. No. 61/249,526, filed Oct. 2009, Crowley.
"Built-in Speed Sensor Records How Fast You Throw the Ball—Used as a Training Aid for Pitchers," Markwort Sporting Goods Company [online], [retrieved on May 22, 2012] Retrieved from the Internet:<URL: http://www.markwort.com/featured/speedsensor.asp>.
"Intelligent Basketball Tracks Trajectory," Freescale [online] [retrieved on May 23, 2012]. Retrieved from the Internet: <URL:

(56) References Cited

OTHER PUBLICATIONS http://www.freescale.com/webapp/sps/site/overview.jsp?code=CASE_STUDY_INTELLIGENT_BASKETBALL>, 2 pages.
"Speed Sensor™ Programmable Balls," Markwort [online], [retrieved on May 25, 2012]. Retrieved from the Internet:<URL: http://www.markwort.com/featured_tab/speedsensor_big.asp>, 2 pages.
Hsu, Michael. "Gear & Gadgets: Making Sense of Your Swing, Turn Your Golf Glove Into a High-Tech Coach." The Wall Street Journal, Aug. 4-5, 2012. (1 page).
Murray, "Freescale Rolls Out World's First 'Intelligent Basketball,'" Design News Blog, Jun. 29, 2007 [retrieved May 22, 2012] Retrieved from the Internet:<URL: http://www.designnews.com/author.asp?section_id=1386&doc_id=215078&print=yes>.
Authorized Officer D. Kim, International Search Report and Written Opinion for PCT/US2010/029068, mailed Oct. 21, 2010, 13 pages.
Authorized Officer RA Kwang Pyo, International Search Report/Written Opinion in PCT/US2009/033831 mailed Sep. 24, 2009, 11 pages.
Authorized Officer S. Baharlou, International Preliminary Report on Patentability for PCT/US2010/029068, mailed Oct. 6, 2011, 9 pages.
Authorized Officer Y. Cussac, International Preliminary Report on Patentability in PCT/US2009/033831, mailed Aug. 26, 2010, 6 pages.
International Search Report and Written Opinion in International Application No. PCT/US2011/050498, mailed Apr. 25, 2012, 9 pages.
International Preliminary Report on Patentability in International Application No. PCT/US2011/050498, mailed Mar. 12, 2013, 6 pages.
International Search Report and Written Opinion in International Application No. PCT/US2013/048958, mailed Sep. 27, 2013, 15 pages.
International Search Report and Written Opinion in International Application No. PCT/US2013/048649, mailed Oct. 22, 2013, 10 pages.
Extended European Search Report in EP Application No. 11824001.9, dated Apr. 3, 2014, 6 pages.
International Preliminary Report on Patentability in International Application No. PCT/US2013/048649, issued Jan. 6, 2015, 7 pages.
International Preliminary Report on Patentability in International Application No. PCT/US2013/048958, mailed Jan. 15, 2015, 12 pages.
Extended European Search Report in EP Application No. 10756993.1, dated Mar. 1, 2016, 7 pages.

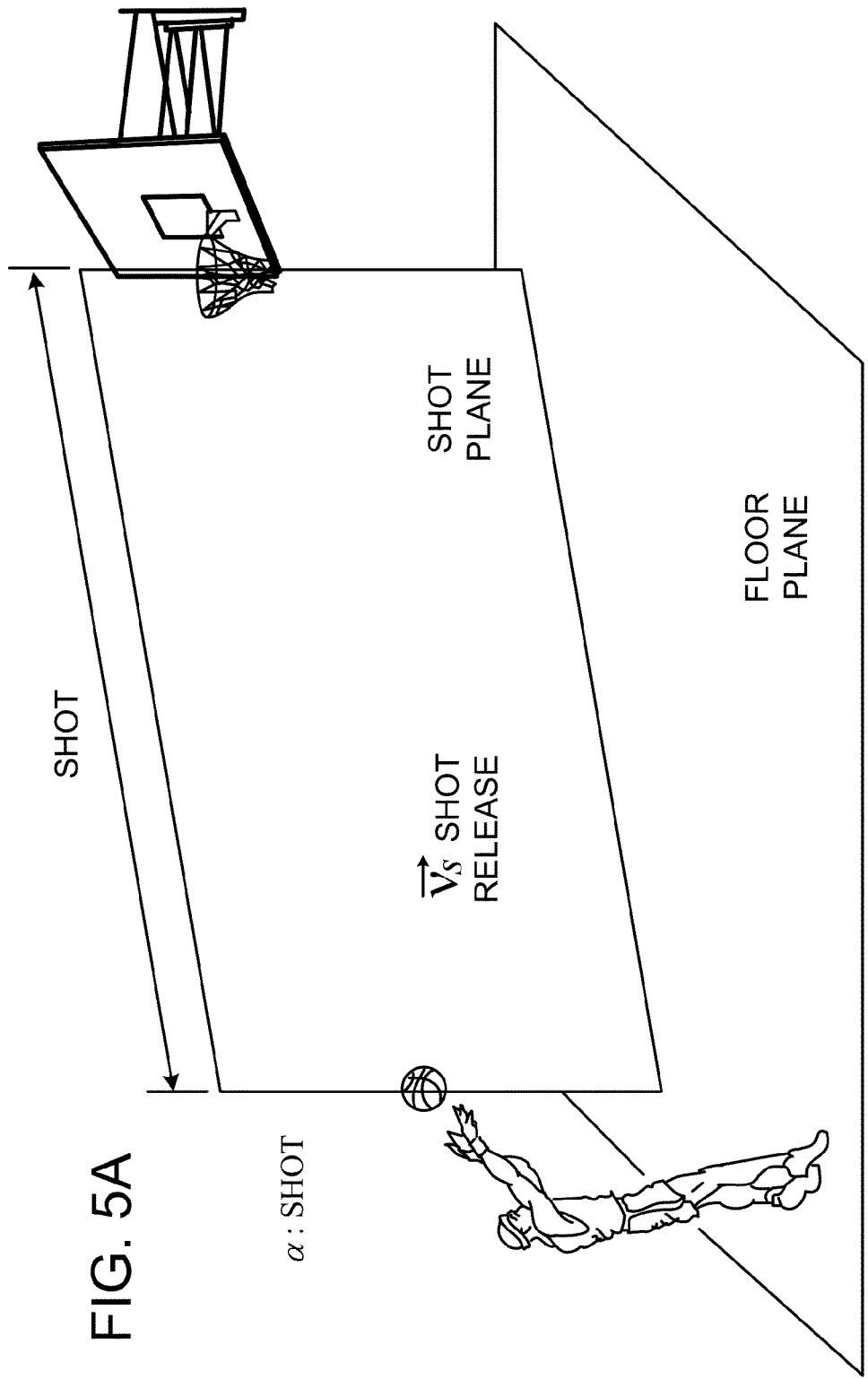

MONITORING OF PHYSICAL TRAINING EVENTS

CROSS-REFERENCE TO RELATED APPLICATIONS

This application claims the benefit of U.S. application Ser. No. 13/961,482, filed Aug. 7, 2013, which claims benefit to U.S. application Ser. No. 13/259,842, filed Sep. 23, 2011, which claims benefit to National Stage International Application No. PCT/US2010/029068, filed Mar. 29, 2010, which claims the benefit of U.S. provisional application 61/164,277 filed Mar. 27, 2009, and U.S. provisional application 61/249,526 filed Oct. 7, 2009. The disclosure of all of the foregoing prior applications are considered part of, and are incorporated by reference in, the disclosure of this application in their entirety.

TECHNICAL FIELD

This document relates to systems and techniques for automatically identifying characteristics of movement of a sports ball during athletic training drills, and of using such monitored motion to make determinations about physical ability of a test subject.

BACKGROUND

Athletics has become an integral part of society, with multiple television channels dedicated to sporting events, with professional athletes promoting all sorts of products, and with the public holding star athletes—both amateur and professional—in high regard, so as to support financial rewards such as college scholarships, sponsorship opportunities, and other revenue-generating careers. With greater general attention on athletics comes greater attention on improving athletic performance. Today's athletes, beginning as early as the elementary school level, specialize in particular areas and train year-round to improve their skills and their conditioning. With athletics leading to a possibly lucrative career for some, and to academic assistance in the form of scholarships to others, more and more athletes have looked to improve their performance in various manners.

Good coaching and personal dedication are some of the best known ways to improve an athlete's performance. A talented coach can often observe subtle problems in an athlete's style of play, and can direct the player to correct those problems. Likewise, a talented trainer can direct an athlete to follow certain regimens to improve physiological weaknesses.

Despite the talent and experience obtained by many top coaches or athletic experts, human perception can capture and fully appreciate only a small subset of the factors that affect an athlete's performance. Thus, despite years of observing how different athletes compete in a given sport or having competed for many years themselves, the most highly skilled trainers and coaches still do not have the ability to quantify very small differences in motion of what they see. These differences in motion can be the most important elements in comparing and diagnosing a player's skill. Also, techniques that rely on human observation and judgment are prone to a high degree of opinion or bias based on the perceptions of any single observer. This bias, and the wide variability of what any given observer believes they are seeing, negatively affects the advice that coaches and trainers can provide to athletes, and also negatively affects the athletes' perception of the advice they are being given (i.e., an athlete may ignore good advice if they think that the provider of the advice does not appreciate their abilities).

In some sports that require a combination of physical athletic skill, muscle memory, and hand-eye coordination skills to be used while simultaneously moving an athletic object, such as a ball, while under pressure situations, the ability to objectively quantify and compare discrete skill differences between players is almost impossible using human perception. The net effect of the inability to standardize the unseen elements of skill has been an over-reliance on only the measurable physical aspects of certain sports, such as athletic speed, strength, and jumping, which causes many highly skilled athletes to be overlooked.

SUMMARY

This document describes systems and techniques that may be used to quantify and benchmark an athlete's current skill proficiency using sensors that capture discrete movements of an athletic device, such as a basketball or soccer ball, while it is in motion so as to link athletic proficiency of the athlete to their ability to control the athletic device, compare the related performance of the athlete controlling the movement of the athletic device to the performance of other athletes that has been aggregated to provide base performance indicators, and to provide feedback for an athlete so that they can improve their performance.

To measure the proficiency of athletic skills, motion sensor devices may be used to monitor the movement of a sports ball to assess various forces that an athlete applies to the ball, such as forces that create acceleration and spin on the ball. Computer systems can measure these forces to recognize patterns of the forces that reflect a degree to which the athlete has trained his or her muscles and hand-eye coordination to apply those forces consistently. Computer-implemented systems can perform a quick and consistent analysis of the sensor measurements so as to create a summary of quantified results for comparative purposes. With algorithms that can analyze the data in a consistent and fast manner, the related output of the devices can be reliably delivered to athletes in a time efficient manner so as to provide immediate and meaningful improvement feedback.

Motion-related data from the athletic device, such as acceleration and rotation data, can be identified and compiled into meaningful samples, and the samples can be compared to a large number of other samples collected in a similar fashion from athletes having known skill levels. For example, the characteristics of athletic performance for a certain action or athletic drill performed while using an athletic device can be determined for each level of play, e.g., grade school, high school, lower level college (e.g., division II or junior college), higher level college, professional, and elite or all star. Sampled data for a particular athlete can then be compared to aggregated data, collected using the same motion sensing technologies and while performing the same drills in the same fashion, from other athletes that were known to be performing at each of these levels, and a level of performance for the particular athlete may thus be determined.

The drills can be predetermined and matched between and among test subjects so that the resulting data can be matched and compared as between individuals in a statistically significant manner. Drills are defined multi-step physical processes that an athlete performs, such as dribbling in a particular pattern, shooting a certain number of shots from a defined point on a court, and running through a pattern, such as through cones or on a line that can be applied to a floor.

As a result, such techniques can provide an indication to an athlete or to recruiting personnel regarding the objective skill level at which the athlete is performing, either for a particular skill set, or overall for an entire sport. In addition, the results may provide constructive feedback by suggesting exercises that the athlete can undertake to improve any deficiencies that the system recognized when comparing the athlete's data to that of other athletes.

While some exercises may simulate actual game-type athletic actions, such as shooting a ball or puck, other exercises may test more general athletic abilities, such as strength, stamina, and quickness. For example, in one test, an athlete may be asked to lay on his or her back and throw a weighted ball repeatedly into the air. The explosiveness of the throw can indicate strength that is relevant, for example, for two-handed basketball passes or blocking by an offensive lineman. The level at which the athlete maintains that level of explosiveness (e.g., as measure by motions sensors such as accelerometers in the ball) may provide an indication of the athlete's stamina for such activity. In another exercise, an athlete may be asked to jump vertically a number of times. Again, a motion sensor may be embedded in a ball and the athlete may hold the ball as he or she jumps so that the explosiveness and stamina of the athlete may be measures. Alternatively, or in addition, sensors may be attached to the athlete, such as in a vest that the athlete wears during an exercise. In a third exercise, an athlete may be asked to perform sit-ups with side twists, and motion sensors in a ball held by the athlete, on the athlete's upper body, and/or pressure sensors on the floor below the athlete may be used to measured the athlete's core strength. Finally, an athlete may be challenged to chest pass a heavy ball from one pylon to another while chasing after the ball. Helpers may place the ball on the next pylon in front of the athlete. Again, the ball may include motion sensors. Such a test may help identify passing strength and running quickness for an athlete.

In certain implementations, such systems and techniques may provide one or more advantages. For example, athletes can be analyzed quickly by completing a number of drills through which the movement of the ball or balls are instantly recorded and easily transferred to a computing system. Also, the systems can record facets of an athlete's performance that would not be observable by a coach watching the athlete, particularly for fast-moving sports that require a combination of athleticism, muscle memory, vision, and the like to succeed. In addition, the analysis provided by the techniques provided herein can be consistent and unbiased so as to provide high quality, objective analysis in a highly scalable system without the need for personal training for numerous observers. For example, motion sensing testing systems can be deployed nationally for operation by technicians who have only limited amounts of training. The analysis, like the data collection, can be unbiased and scalable, so that it can give an athlete a fair evaluation without concern that assertions of favoritism will be made, and can be completed without needing to train numerous analysts as a system grows.

The details of one or more embodiments are set forth in the accompanying drawings and the description below. Other features and advantages will be apparent from the description and drawings, and from the claims.

DESCRIPTION OF DRAWINGS

FIGS. 5A and 5B show parameters that can define a basketball shot.

Like reference symbols in the various drawings indicate like elements.

DETAILED DESCRIPTION

Figure 1A:
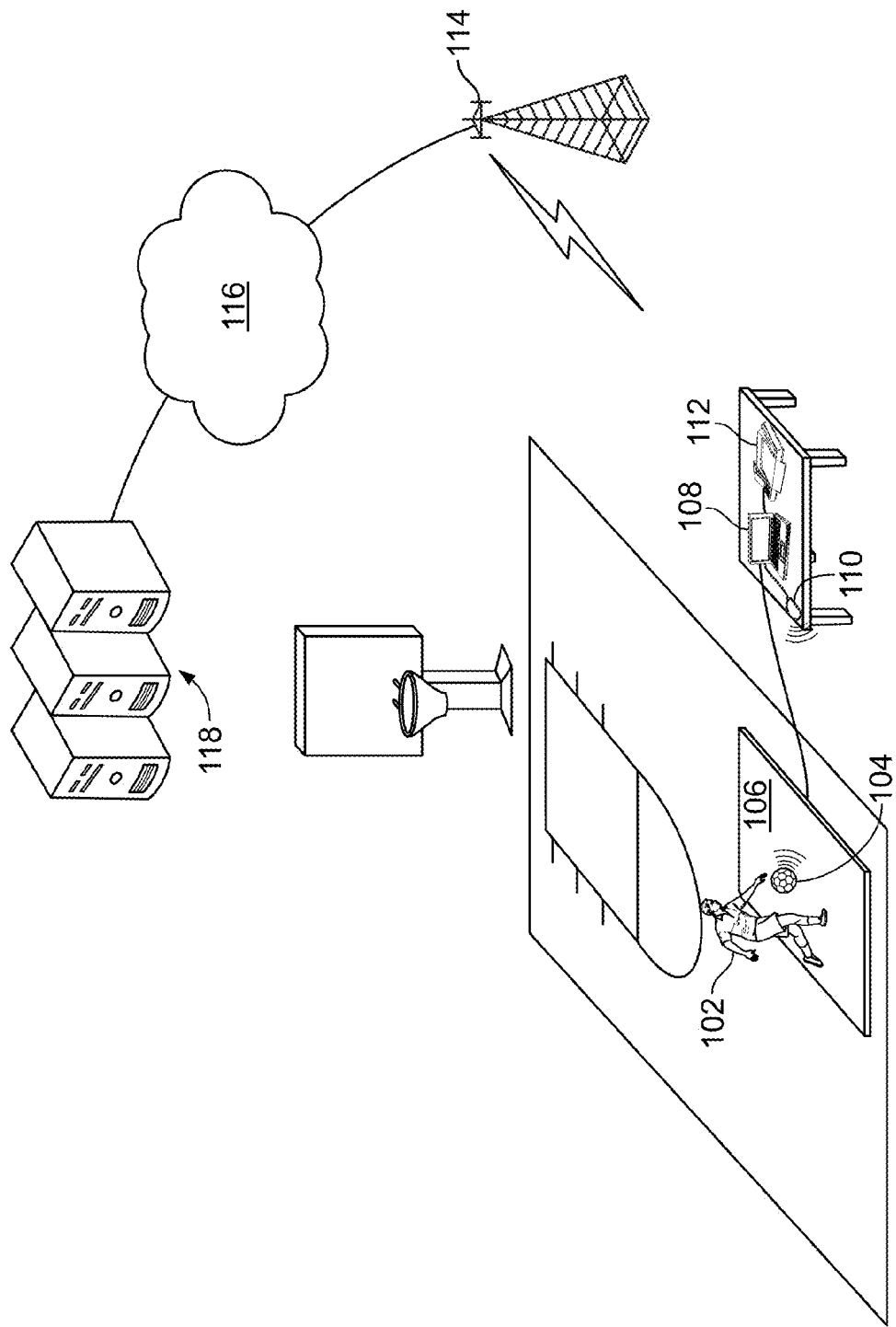
FIG. 1A is a conceptual diagram of a system for electronically measuring athletic performance and providing feedback on the performance.

This document describes systems and techniques for capturing and evaluating athletic performance in a repeatable and objective manner by measuring athletes who have been instructed to perform certain drills that match drills that other athletes have also performed. In general, a sporting device such as a basketball or other ball can be provided with, or be observed by, motion sensors, such as accelerometers and angular rate gyros, to record data about the manner in which an athlete manipulates the sporting device. Additional data may be captured from the athlete, such as via laser-based motion recorders, pressure sensitive pads, and shoe-based sensors. The athlete may be directed through one or more drills, such as a dribbling or shooting drill, and his or her actions may be recorded through the various sensors as they complete the drill. The drill may be well defined so that the data that is captured may be compared to other instances of the drill, including instances in which the same athlete performed the drill at different periods of time, and instances in which other athletes performed the drill.

The motion data may be captured on a computer system in proximity to the location where the athlete performed the drill. The capturing of the data may occur, for example, via wireless communication between a sensor assembly inside the sporting device and a wireless transceiver attached to a computer, such as via a USB port or similar interface. The motion data may then be transformed, sampled, and converted in various manners and may be compared to data from other athletes that has been aggregated for later statistical or similar analysis. The other athletes may have provided indications about their level of athletic performance, such as whether they are varsity high school players, junior college players, division I players, professional players, or other levels of player. If those other athletes performed the same or similar drills under controlled conditions (by being instructed by, and observed by, a technician to ensure that they follow the appropriate steps of a drill), their aggregated data can be compared to the data for the first athlete to determine where, on a continuum of skill levels like that just described, the athlete falls.

Such an analysis may be simple, such as by being based on a single drill, or it may be complex and involve a large number of drills that test a variety of skill sets for an athlete. The simple testing may be conducted as an initial test to see if an athlete is interested in further testing. For example, testing may be provided at a public event like an AAU tournament or a 3-on-3 basketball tournament. More complex testing may also, or alternatively, be conducted. For example, athletes may attend more extensive testing at fixed athletic facilities, such as facilities that are relatively common in major metro areas. The additional testing may test a variety of drills that include tests for ball handling, jumping, shooting, and other similar skills.

The analysis may involve identifying individual sub-events within a drill, such as individual instances of a basketball bouncing off the floor and entering/exiting an athlete's hand. Such sub-event may be identified by running a time-wise window across the motion data recovered from a drill, and looking for sudden accelerations or other changes that may represent palming or bouncing. The analysis may also involve isolating instances in which the athlete has lost control of the ball, such as by identifying the absence of an adequate acceleration in a particular time window (thus indicating that the athlete let the ball bounce multiple times without dribbling it and/or was required to dribble the ball at a low height and high frequency to regain control over it).

The test results may be generated at a central facility that is remote from the various test centers. Such an arrangement may permit easy deployment of the system, with sensor-fitted balls and wireless transceivers being the only hardware that needs to be sent to remote sites in many implementations. Client computers such as laptop computers may be provided by a technician, and may communicate with a remote server over the internet, including through a web browser that can have a downloaded plug-in for controlling communication with the sporting device and for uploading the gathered information to the server.

The server may in turn include a web server, and the client computer may receive information back from the server in the form of an XML and/or HTML document that can be shown or otherwise provided to the athlete, with a summary of the data that was reviewed for the athlete, and a list of instructions and exercises for the athlete in order for the athlete to address any weaknesses that were indicated by the testing.

Athletes may also be encouraged to conduct testing at multiple different time periods. Such testing may measure the relative progress that the athlete has made. Such relative progress may also be compared to aggregated data on the progress of other athletes. The evidence of progress for the particular athlete may be fit in a number of known mathematical and statistical manners so as to produce a prediction of the athlete's near term and longer term expected progress if the athlete continues at a pace of development that matches the development measure for other athletes of similar progression.

Referring now more particularly to the figures, FIG. 1 is a conceptual diagram of a system 100 for electronically measuring athletic performance and providing feedback on the performance. The system 100 generally includes a sub-system that is local to one or more athletes who are being tested, and a sub-system that is remote from the athletes and includes one or more servers. Although a separated system is shown here, all of the processing for the system may also be localized at a single location.

A separated system may provide a number of advantages, however. For example, it may eliminate the need to deploy and maintain computers and software in the field. Rather, only limited technology, such as one or more sporting devices (e.g., balls, shoes, clubs, etc.) need be sent out, and software may be downloaded to computers (such as laptop computers) that are already in the field, such as via a web browser plug-in that manages communications with the sporting device and uploads device data. As a result, a company operating the system may reduce its capital costs significantly by using computers that are already owned by field personnel and are being used for other purposes. In addition, the company can better control who is using its technology, by maintaining ownership, for example, of the sporting devices, so that a field representative must return the device when their term of representation is over. Also, when field deployment of software occurs via download over the internet, a company can push out the programs more easily, and may also keep them updated regularly with little effort. Moreover, such a separated system permits the company to maintain better control over its analysis code so that the code is not easily taken and provided to a competitor, and so that it can be updated and kept fresh in a very controllable manner.

A hybrid approach to splitting the duties of the in-field sub-system and a central sub-system can also be pursued. For example, a client device such as a laptop computer may be provided with code and data that is sufficient to test an athlete in one entry-level drill, such as dribbling a figure eight. Such distribution of basic testing code may permit the testing to occur more quickly and reliably than if a round-trip to a central server were required. Such reliability can be important for entry-level testing also, because frequently such testing would occur at various festivals and tournaments that are far from dedicated IT equipment.

In the hybrid system, the server system could be used for subsequent and more extensive testing, after athletes have been introduced to the system and have decided they would like to receive additional testing and guidance. In this manner, the system 100 can be introduced conveniently to athletes and they can be given an inexpensive trial of the system's capabilities with the entry-level drill. Although security may be compromised for testing of the one drill (because the analysis code will have been sent to remote client devices), a competitor could not make much from the one drill in any event, so the risk to security is minimized.

In FIG. 1, the local computer sub-system is made up of a laptop computer 108, a wireless transceiver 110, and a printer 112. The computer 108 may take other forms and may be loaded with software to cause an athlete's data (from the measured motion of a sporting device that the athlete manipulated and/or other sources) to be analyzed, and may cause reports to be provided to the athlete. The computer 108 may be loaded with native applications to receive such input and produce such reports, and to also analyze the input data with respect to similar data from other athletes. Alternatively, the computer 108 may be loaded with basic workplace applications, such as a web browser, and the system 100 may provide a downloadable plug-in for the browser that will control communications with the transceiver 110 and with a server.

The transceiver 110 may take a variety of forms, and may be directed to capturing motion data from a sporting device in the form of a basketball 104 in this example. The basketball 104 may be of a common size and shape, and may contain a sensor assembly that includes accelerometers and angular rate gyros mounted inside it, in a way that does not interfere substantially with the handling of the ball, to capture motion of the ball 104 in a manner that is usable to the system 100. The transceiver 110 may in turn communicate with the computer 108 in a familiar manner, such as through a USB port or the like, so as to make relatively simple the use of the computer 108 with the system 100 to capture motion data.

The printer 112 is shown as an example of one way in which a report on an athlete's performance can be presented to the athlete. For example, certain numerical figures or graphs may be generated to visually show where the athlete scores on a continuum of skill levels. In addition, recommendations may be generated in a textual format to be given to the athlete, with particular instructions on how the athlete can improve their performance, including suggested exercises or drills to perform in order to improve the athlete's muscle memory for a particular task. For example, if the testing of an athlete indicates that the athlete does not release the ball during a dribble with adequate velocity, the system 100 can recommend drills and conditioning routines to address such a situation.

In addition to being provided on paper from printer 112, information may be provided to an athlete regarding his or her performance via other mechanisms. For example, data for an athlete may be copied to a thumb flash drive or other similar mechanism. The athlete may then return to a next testing session and provide the memory mechanism for use in comparing the athlete's skills at an earlier time to their current skills, and extending out any recognized trends to give the athlete or someone reviewing the athlete an opportunity to see if the athlete is similar in skills to other athletes who have excelled over time, or have stalled and fallen behind comparable athletes.

The data for an athlete may also be stored in the system 100, and the athlete may provide identification information in subsequent visits so that prior test data for the athlete is joined with subsequent test data. Access to data may be provided to the athlete via a message sent to the athlete (e.g., via text message or e-mail) or by providing the athlete with log in credentials to a central site. A combination of such methods for provided the athlete with access to the data may also be employed. In addition, reporting tools may be provided under any of the examples above, so that the athlete may return home and produce custom reports and otherwise manipulate the data on their performance.

An athlete 102 is shown in FIG. 1 dribbling the basketball 104. For example, the athlete may be instructed to dribble the ball in a figure-eight pattern several times, or for a fixed number of times so as to record a statistically relevant sample of items to record and analyze, while motion data is being captured by sensors in the basketball 104 and perhaps via other sensors. The athlete is also shown as performing on a pad 106. The pad 106 may be pressure sensitive and may provide additional data that may be coordinated with the motion data from the sporting device 104. For example, the relative timing between up and down motion of a ball and contact timing of a basketball player's feet may indicate certain room for improvement in the athlete's skill set.

In addition, other sensors may be employed along with the sensors in the sporting device, such as laser location finders that may indicate the relative positions of points on the athlete's 102 body, or motion data of the basketball 104 that cannot be fully captured by sensors inside the ball. Certain sensors may also identify information relating to the actual time that a drill starts and stops, or how quickly an athlete moved from point A to point B while simultaneously controlling the athletic device, how consistently the athlete handles the ball, the variability between dribbles, etc. Also, sensors may be used to determine athleticism, such as in vertical jump tests, both to measure the height of the athlete off the ground and to measure the acceleration of the athlete off the floor.

The sensors may generate a variety of data types. The sensors can measure athletic stride, number of impacts, change of direction, etc, while sensors in a ball would capture the muscle memory skills associated with handling the ball while moving in very quick and short bursts. Also, the timing of data for various sensors may be aligned and synchronized so as to deliver more information on the athlete's performance. For example, laser-based sensors, when combined with in-ball sensors, may provide an indication when a player loses a dribble during a drill, even in situations where either sensor group alone would not make the same determination.

Sensor-equipped specialized athletic devices that differ from the corresponding devices that are used in competition may also be used for testing athletes. For example, sensors may be provided in a weighted ball, and an athlete may be directed to execute drills that can deliver predictive or diagnostic data on a player's core strength. For example, the heavy ball can be thrown, and the sensors can capture acceleration, distance, and speed. As another example, an athlete can perform a series of repetitive drills with the torso, such as situps. The sensors can measure force, acceleration or other movements, the average and median of these measurements, and any degradation of these elements over the course of the entire drill. These measurements can be used to benchmark, compare, and predict core athletic strength that is critical in many sports.

Certain of the information may be compared to aggregated data for other athletes, while certain data may be provided in a form that does not involve such comparison. For example, drill data for particular skills may be compared to drill data for other athletes, while core strength measurements may simply be provided in raw form or in some revised form (e.g., on a scale of 1 to 10) but without the need to place such numbers into some preexisting skill level relative to other athletes. In this manner, various sorts of data may be made available for review by an athlete or by others from a single location—whether the particular data is best presented in comparison or as an absolute.

The local client sub-system may be connected to the server sub-system through a wireless connection, such as an aircard or similar structure or a WiFi card and WiFi hot spot. A network 114, such as a cellular data carrier network 114 may transfer the data and communicate through a network 116 such as the internet, to the server sub-system shown here as a single server 118, but which could include a large number of servers to receive various types of requests. The server 118, as described in more detail below, will have previously been provided with data reflecting skills for a number of other athletes who already ran the relevant drill or drills. The previously processed data will also indicate the skill level of several of the athletes.

The server 118 can thus compare the data representing the performance of one athlete acquired by the client sub-system, to the information that is aggregated for performances of a group of other athletes whose relative levels of development are generally known. The server may then return to the computer 108, through the networks 114 and 116, information that can reflect such a determination and provide additional helpful data and advice to the athlete. For example, the computer 108 may be used to print out a number of pages of mark-up language material (e.g., HTML) that include data and graphs to show the athlete what was measured from them, and what comparable values have been observed for players from various levels of a sport. In addition, various instructions can be provided in a similar manner, which the athlete can take home with them and read to improve a particular skill set or drill. Such data and reports may be provided via printer 112, or via an electronic file such as an HTML or PDF file stored to removable portable media that is given to or provided by the athlete. For example, a sponsor at an athletic event may supply free flash memory containing the sponsor's name, and the data for an athlete may be stored onto the flash memory by attaching the flash memory in a well-known manner (e.g., through a USB port).

An athlete can also capture data to be used in customizing a videogame experience. The athlete can first perform a variety of drills to obtain statistics indicative of their overall current skill levels in a sport. They may then have the figures loaded to portable memory devices that can be used with videogame systems, whether console or PC. Such athletes may then load the data to a game that involves athletic performance that uses the skills tested by the athlete, and their character or avatar in the game may perform according to their actual real-world skill level, with multiple different variables being identified to define the full performance palette for the athlete. In this manner, friends may set up head-to-head battles in sporting games, where their own personal skill levels affect how the simulated videogame contest will turn out. The athletes may also thus be motivated to return for additional testing after they have practiced so that they can have better baseline skill numbers that will improve their performance vis-a-vis other players in the game.

Figure 1B:
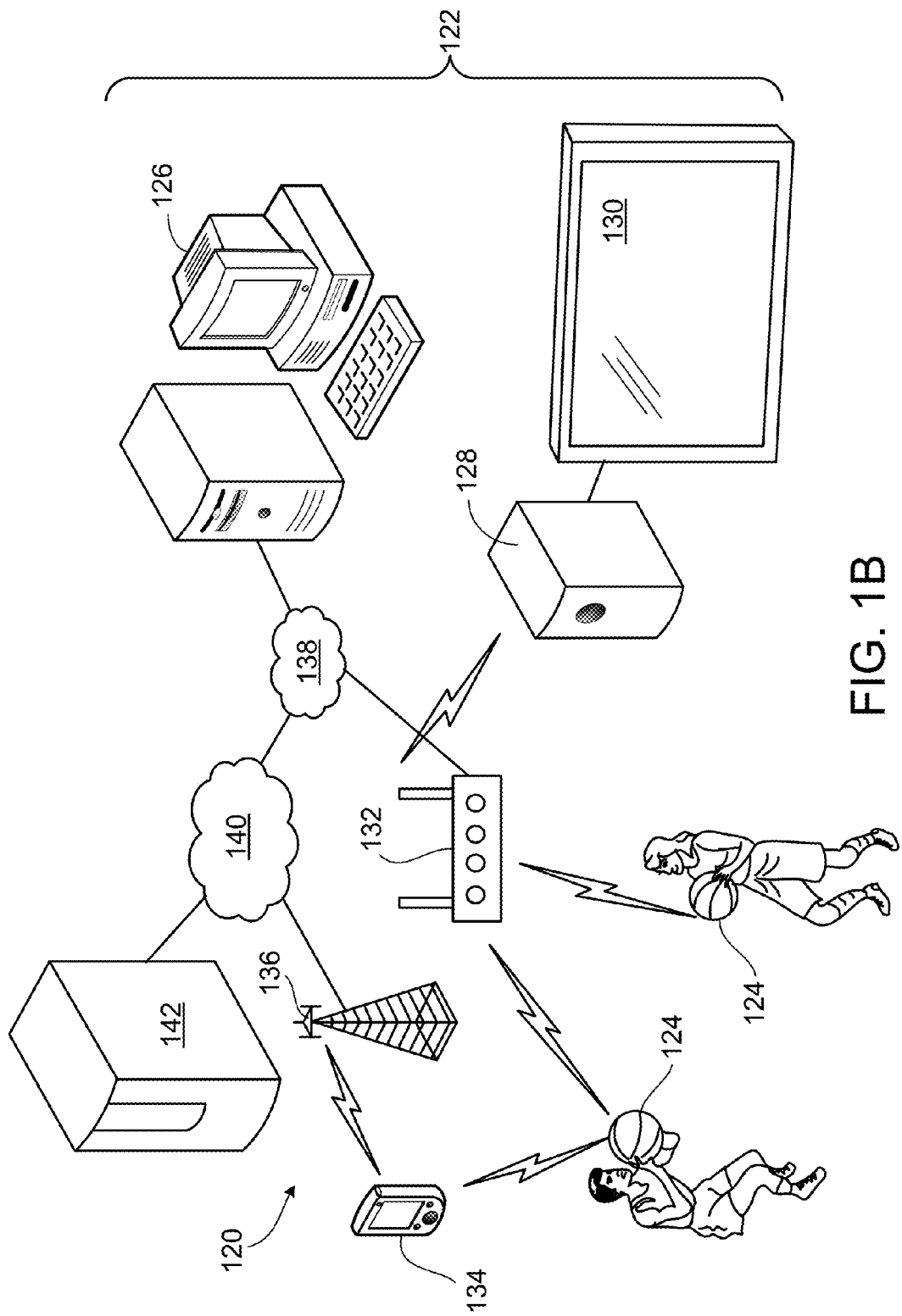
FIG. 1B shows a system for interfacing sensored sports balls to a home consumer electronics system.

FIG. 1B shows a system 120 for interfacing sensored sports balls 124 to a home consumer electronics system 122. In general, the system 120 may be used to permit a consumer to practice with the sports ball, such as in their driveway, and then immediately enter their home and have data regarding their skills uploaded to their personal computer, console gaming system, or mobile computing device (e.g., smart phone or app phone).

Figure 8:
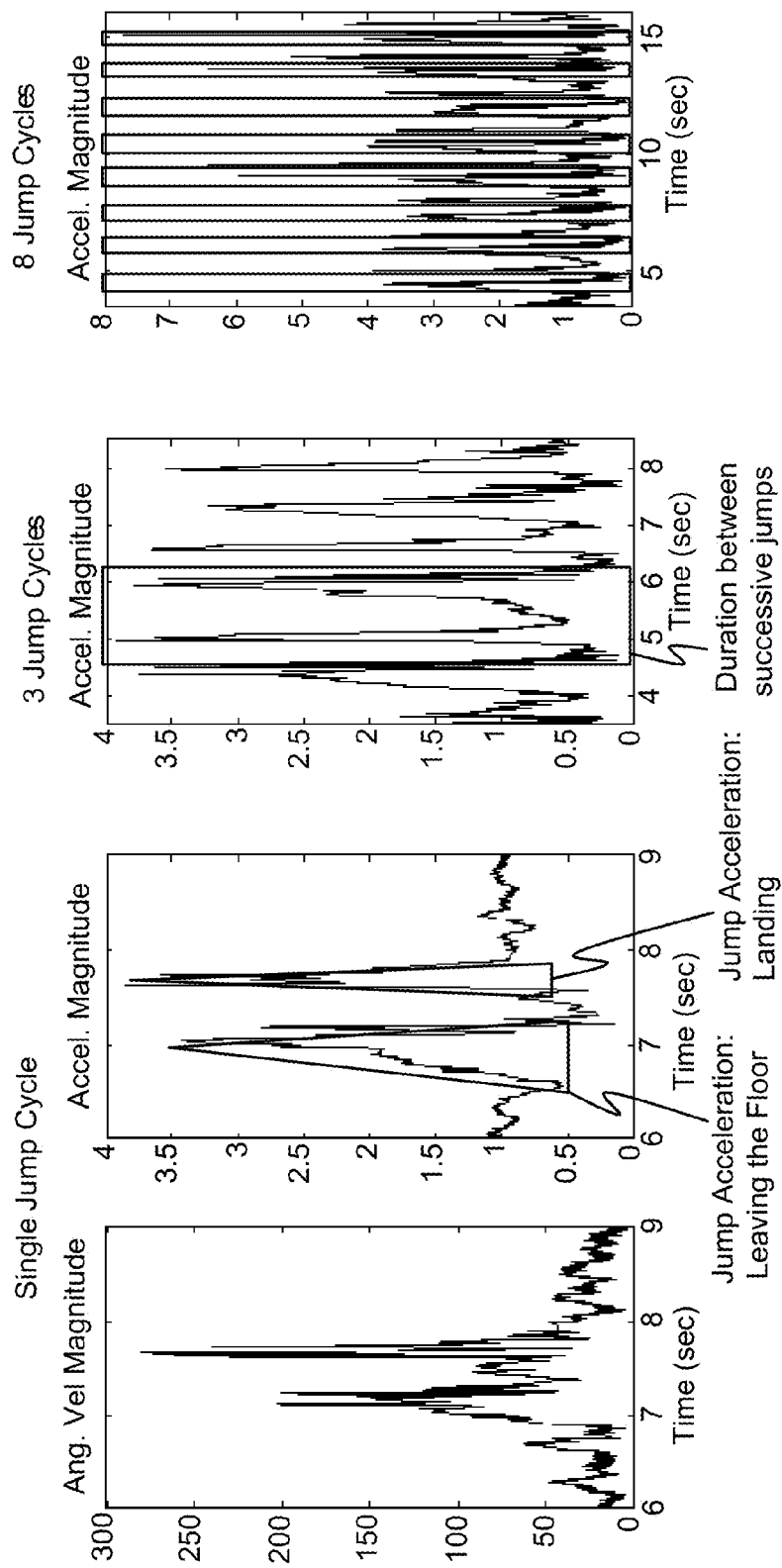
FIG. 8 shows example motion data from a jumping subject.
Figure 9:
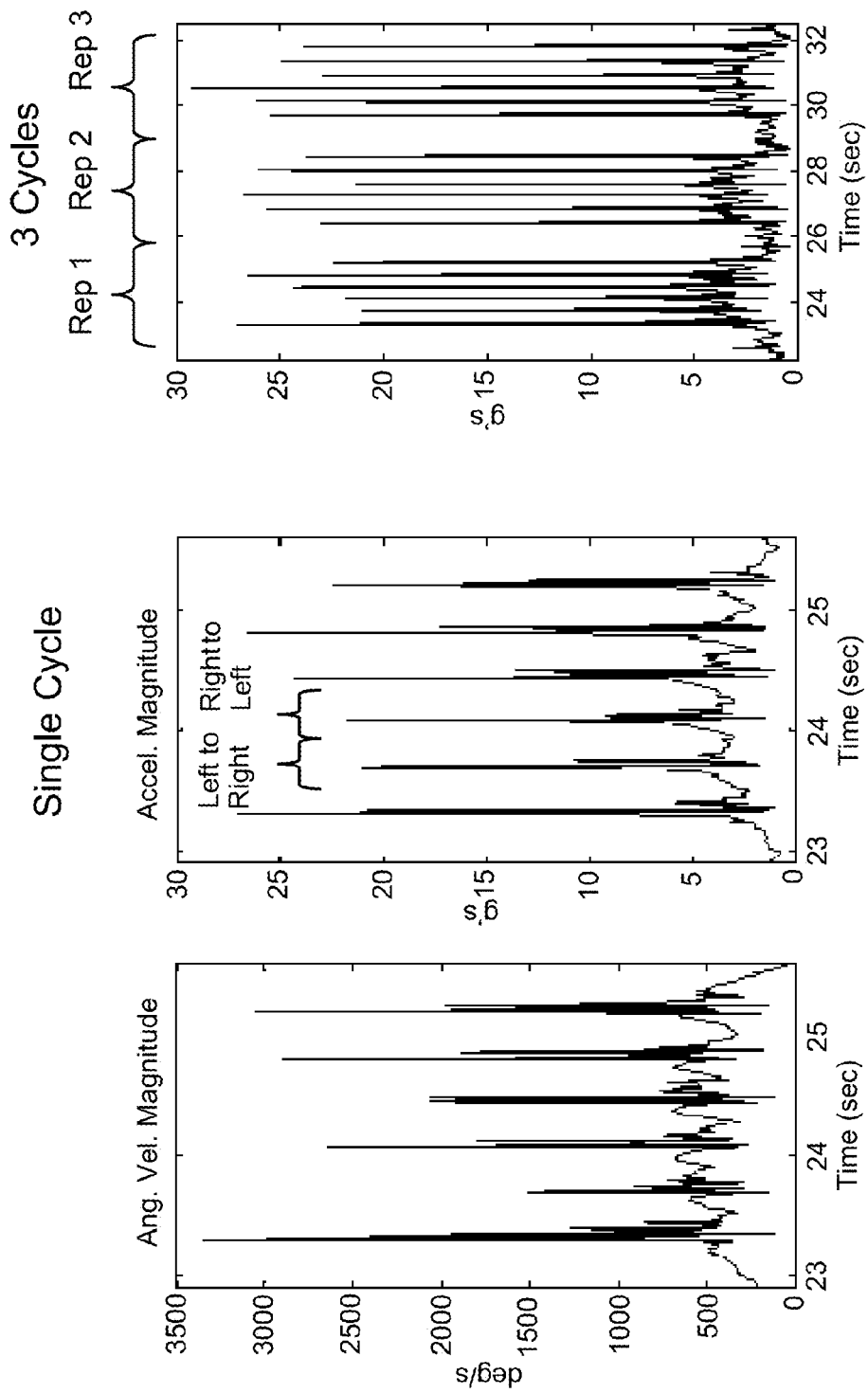
FIG. 9 shows example motion data from a subject performing sit ups with side taps.
Figure 10:
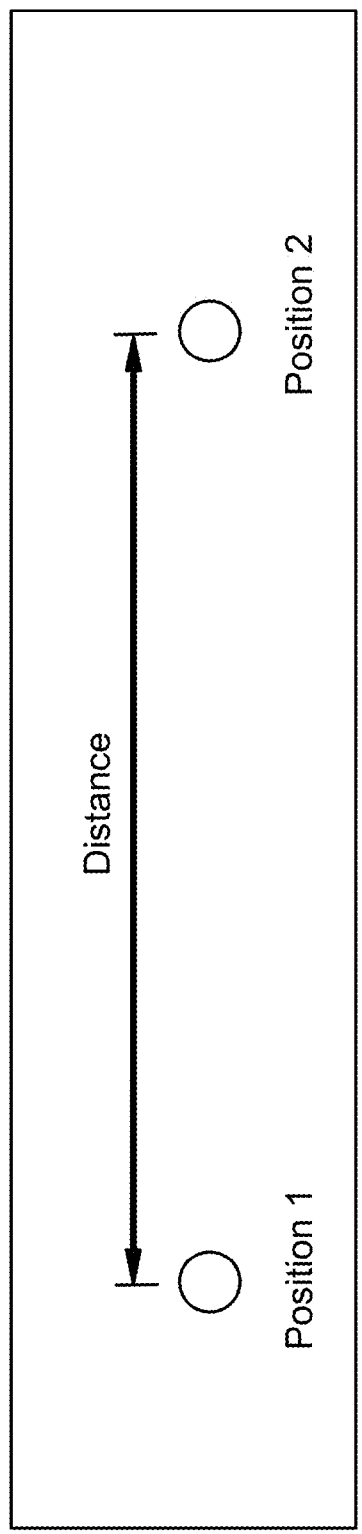
FIG. 10 shows schematically a set up for a throwing and running drill.
Figure 11:
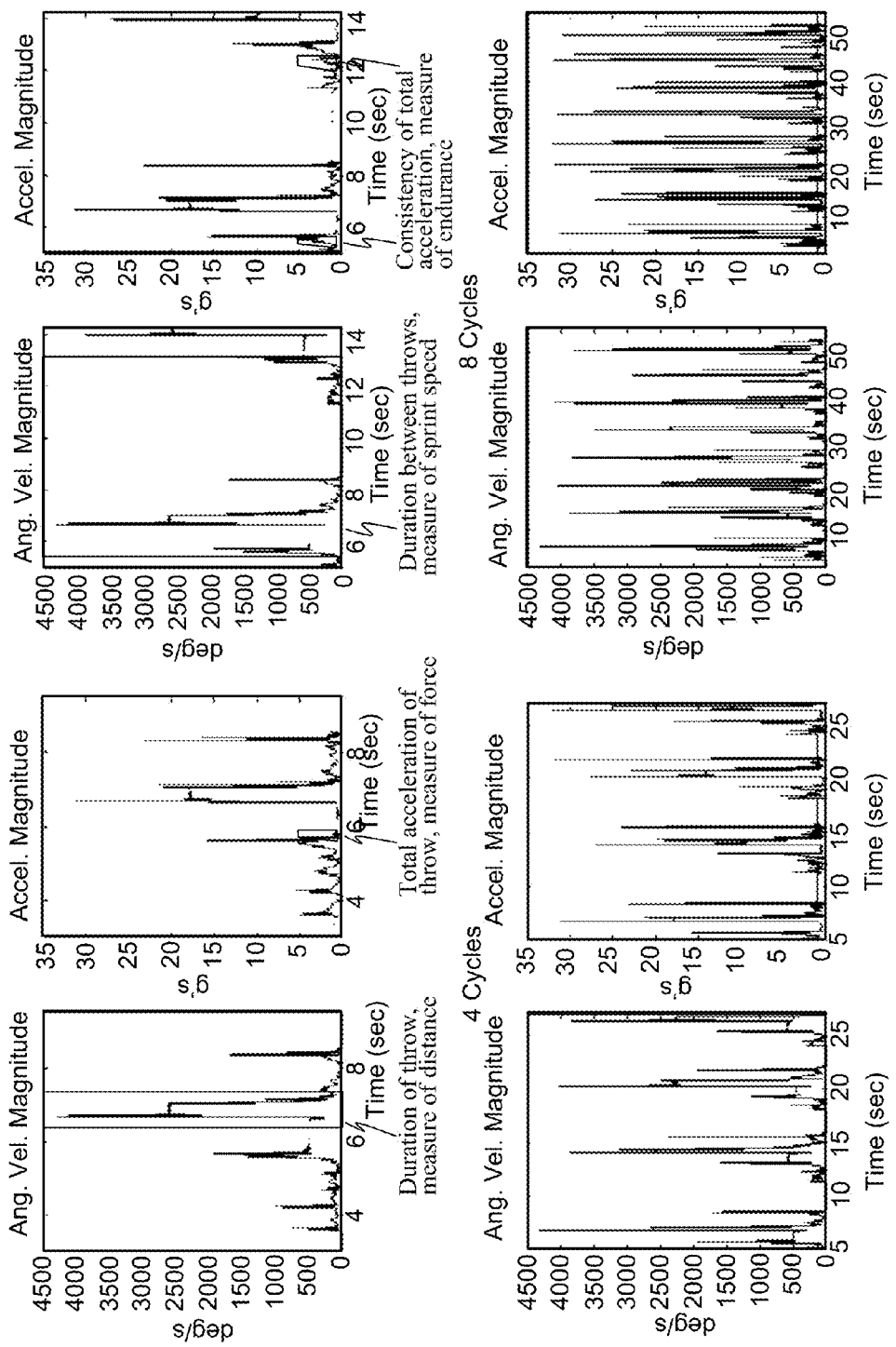
FIG. 11 shows motion data for a repetitive throwing and running drill.

In the figure, two athletes each hold one of the balls 124, which in this example are basketballs. Each of the athletes may have just finished completing a series of drills, such as performing dribbles in a FIG. 8 through the legs, performing dribbles around the body in a circle, dribble while running through certain forms, and the like. Each athlete may perform one drill at a time, or may use materials such as a guidebook to perform drills or exercises in order, and the balls 124 may store motion data, such as in the manners discussed above and below, for each such drill. Separators may be provided between sets of data for each drill so that distinctions between each drill may be determined during later data analysis.

As shown in the figure, electronic assemblies inside each of the balls are communicating data wirelessly either with a smartphone 134 or a wireless router or switch 132. Such communication may occur in familiar manners, such as by using standard BLUETOOTH or WiFi protocols and mechanisms at each of the devices. The balls can announce themselves after a set period of inactivity has expired after drills have been performed, may perform a handshaking process, and may begin uploading whatever information they have obtained from the motion of the balls 124 during the drills. The smartphone 134, a personal computer 126 (e.g., a laptop, netbook, or desktop computer), or a videogame console 128 (e.g., a MICROSOFT XBOX, NINTENDO WII, or SONY PS/3) connected to a video display 130 (e.g., a high definition television) may be the destination of the data and may include software for storing the information about the motion of the balls 124 and further transmitting such information (perhaps after some level of reformatting) or analyzing the information.

The consumer electronics system 122 may include each of the consumer electronics devices discussed here (e.g., console gaming system 128, smartphone 134, or personal computer 126), which may in turn communicate over a local area network 138, which may be partly wired (e.g., IEEE 802.3x) and partly wireless (e.g., IEEE 802.11x).

One or more of the devices may also communicate through a larger network, including the internet 130 with a server system 132. Such a server system 132 may provide functionality like that discussed above and below for analyzing an athlete's performance data, including by comparing it to performance data for other athletes. Such information may be processed, and the results may be downloaded back to one of the consumer electronics devices, including through wireless network 136.

In operation of the system 120, the two athletes may each have a ball 124 or may take turns with a ball, and may, for example, go outside in a driveway while performing a number of drills that may be outlined on a paper card one of them received with a videogame (where the instrumented, or sensored, ball may have been integrally packaged with the game disk, cartridge, or download code). They may each perform the requisite drills with the ball or balls 124, and then upload data that represents motion data for their drills to one of the consumer electronics devices 126, 128, 134.

In one example, such data may be further uploaded to the server system 132, which may analyze the data and provide information to each of the athletes that explains to them, such as graphically or in tabular form, how they compare to each other and to other athletes in terms of basketball skills that are reflected by the drills they performed. Other uses of the information may also be made, such as described above and below.

Alternatively, or in addition, the data from the balls 124 or data produced from such ball data and that reflects information about the athletes' performance in the drills, may be provided to one or more of the consumer devices 126, 128, 134. Such devices may be loaded with a sports videogame that permits competition against a computerized opponent by an avatar controlled by the player, or head-to-head competition between two players. The data may thus be used to affect the athletic performance of each players/athlete's avatar. For example, if the data from the drills indicates that the first athlete dribbles strong with the right hand, the athlete's avatar in the video game will tend to go stronger to the right. Such provision of the athlete's ability to the avatar may be absolute or relative, or a mix of the two. For example, if the test data shows that the athlete's skills are horrible, their avatar may also be horrible in a videogame. Alternatively, the general skill level of the athlete may be raised to some even norm with that of the other players, and the relative strengths of the player may be emphasized. For example, perhaps the athlete was horrible going right and even worse going left. In such a situation, their avatar might play as going strong to the right and normal to the left, with an average ability that matches that of the second athlete so that the videogame is evenly matched. Nonetheless, absolute skill levels have benefits in that they encourage athletes to improve their overall skill level and to get better at playing the game in real life, in the process.

Figure 2A:
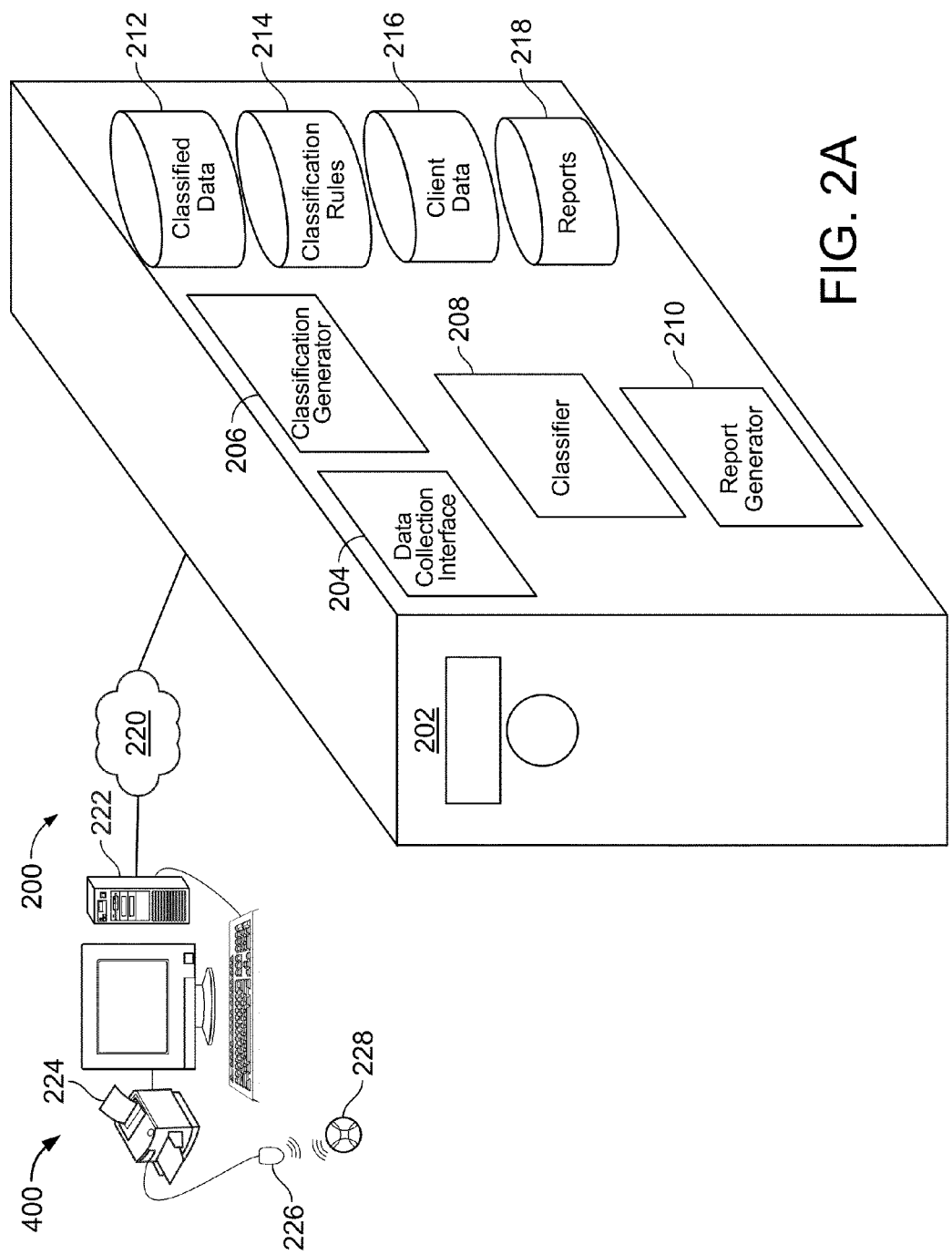
FIG. 2A is a block diagram of an illustrative computer system for comparing performance indicators for an athlete to aggregated performance indicators for a plurality of other athletes.

FIG. 2A is a block diagram of an illustrative computer system 200 for comparing performance indicators for an athlete to aggregated performance indicators for a plurality of other athletes. In general, the system 200 is similar in arrangement to system 100 in FIG. 1, but more detail is shown here about a server system 202 that may be used to provide evaluation data for athletic performance.

Starting at the client side and then moving to the server system 202, there is shown a sporting device in the form of a basketball 228, which may communicate motion data that is measured by sensors inside the basketball 228 with a wireless transceiver 226. The wireless transceiver 226 may in turn provide the motion data to a computer 222 that may pass the information to a network 220 such as the internet and/or a wireless network like a WiFi network or cellular data network, and on to the server system 202. The computer 222 is also provided with one or more output devices in the form of a printer 224 and computer monitor, and may also have ports for writing to portable memory devices carried by athletes who are tested by the system 200. The client-side system in this example can be operated in a manner similar to the system 100 described in FIG. 1.

On the server side (which again, may include one or a number of server computers, including web servers, database servers, and other computers), the server system 202 includes a number of components to assist in processing data regarding athletes' performance in a number of drills. (which may be among a number of additional components that are omitted here for clarity)

First, a number of data stores 212-218 hold data that is relevant to the athletic evaluation functions. For example, a classified data store 212 includes information from past athletes whose performance data has been generated and who are classified into certain skill levels. The data may be aggregated from across a large number of athletes so as to make the data meaningful. Also, each set of data may be correlated to a particular drill or exercise performed by the athlete, so that the data can be properly compared to data for other athletes that performed a matching drill or exercise. (A matching drill is a drill that is the same as a first drill or that includes some substantial superset or subset of the first drill.)

Classification rules dataset 214 may store data representing rules that are derived from analyzing the classified data, and may include heuristic rules or other rules to apply to incoming data to determine an appropriate skill level of an athlete who generated the data. For example, a set of rules may be combined to determine a skill level of a free throw shooter, such as the number of times a free throw rotates and the hang time and entry angle of a free throw.

Client data store 216 may store two or more types of data. For example, it may store information about the particular client computer 222 that is sending testing data to the server system 202, such that an account associated with the computer 222 or with a login made through the computer 222 can be debited. Such debiting may occur where an operator of the client system collects money for providing the testing services, and some of the money is to then be provided to the organization running the server system. In such a manner, the central system may best be able to audit the operations of field personnel and to track accounting functions properly (because it will know the number of transactions). The client data may also relate to athletes that have used the system 200. Such client data may include raw motion data that has previously been uploaded in combination with an ID for the particular athlete, in addition to a history that summarizes tests and drills the athlete has completed, and reports and recommendations that have previously been provided to the athlete. Storing such data may permit the system 200 to provide ongoing support to an athlete as they develop, including by providing reports that show past progress of the athlete at certain tasks, and projections for the athletes' development with respect to those tasks.

A reports data store 218 stores formats for various reports that may be provided to athletes or advisers to athletes. The reports may take a variety of forms, such as tabular data comparing an athlete to other athletes or groups of athletes, graphs making similar comparisons, and textual reports providing recommendations for drills and exercises that an athlete may undertake to improve his or her performance. In addition, the reports can include tracking modules that can be downloaded to a portable media owned by the athlete, where the athlete may track developmental milestones using the modules. For example, an athlete can enter the completion of certain exercises and the results of exercises that the athlete has completed, and the module may communicate with the system 200, either immediately (e.g., to schedule follow up testing when the athlete's results indicate that they may be ready to enter a new level of development) or the next time the athlete comes in for testing. Tracking actual activity of the athlete may improve the advice given to the athlete. For example, if the data indicates that the athlete has worked very hard on a particular skill set or muscle group, but is not showing development at a sufficient level, the routine for the athlete may be changed by identifying the athlete as sharing characteristics with a different group of athletes who previously responded poorly to one routine, but responded better to a different routine.

Other components shown in the figure provide particular functionality for the server 202. For example, a data collection interface 204 may obtain uploaded data about athletic performance form the computer 222. Such an interface may take a variety of forms, including as a web server that serves forms that a technician may fill out for each athlete (e.g., to include identification information and information about the drill or drills performed by the athlete), and that include selectable controls that cause data from the basketball 228 to be gathered and then uploaded to server system 202.

The data collection interface 204 may also screen uploaded data to ensure that it matches an appropriate profile for any particular drill that the data supposedly represents. For example, the interface may test to ensure that the data represents a long enough time period, an appropriate number of dribbles, appropriate motion data for the drill (e.g., there should be some bouncing for a dribbling drill), and may provide an alert back to a technician (e.g., to repeat the testing) if the data does not appear to be proper data.

In addition, the data collection interface 204 may reformat the data in various manners, such as those described below with respect to FIGS. 3A-3C. For example, the interface 204 may identify individual sub-parts of a drill such as individual dribbles in a basketball drill. The interface 204 may then convert raw motion data into other forms, such as parameters having particular values that represent a user's performance. The parameters may include figures that reflect average times for a ball to stay in a user's hand, average time between dribbles (and variation in the same), and other such parameters. Other components may also take on the role of initially processing incoming raw motion data in order to make it easier to process and to compare between one athlete and another.

A classification generator 206 develops rules for placing athletes into particular rankings or classifications relative to other athletes of known classification. The rules are selected so as to provide statistically predictive indicators of real athletic performance that can be derived from motion data and other data compiled from athletic drills. The classification generator 206 may, for example, receive motion data from a large plurality of athletes who have been classified as falling into particular skill levels. The classification generator 206 may analyze the data in various known mathematical manners to identify correlations between data points for athletes of a particular skill level or similar skill levels. For example, the classification generator 206 may recognize that athletes of a particular skill level frequently dribble a basketball according to a particular time pattern, or that the ball spends a certain amount of time cradled in their hands during a dribbling exercise. Where the athletes provided their data in a controlled manner by conducted a predefined and repeatable drill, such correlations can be determined to have significance, and can then be made into classification rules by the classification generator 206.

The rules for classification may also be generated with manual input. For example, an operator of a system may determine particular aspects of performance that have been correlated with an athlete's skill level. They may then test a number of athletes at known skill levels to identify values for that aspect of performance at each skill level (and to confirm that there is a correlation between the values of the aspect and skill level), and may store the measured figures for that aspect of performance.

A classifier 208 in the system 200 uses such rules, in whatever form they may be provided, to classify future athletes according to the strengths, abilities, and weaknesses. The classification may occur according to heuristics, by a degree-of-match determination across multiple factors to corresponding data for athletes of known skill level, or by other acceptable mechanisms. Such classification may occur by obtaining data relating to measured motion data for a new athlete in predefined drills that correspond to the drills performed by the prior athletes of known skill level.

The classifier 208 may also include a trend analyzer that may correlate an athlete's data at different points in time, to the performance data of other athletes at different points in time. Thus, the other athletes may have been tested over time, and may be provided with identification numbers so that the different testing can be matched (though the identities of the athletes themselves may be anonymized). Various trending techniques may be performed to find prior athletes who trended in particular manners for one skill or a predefined group of skills that has been determined to develop in parallel. The new athlete may also provide information about their skill level, which information may be fed back into the system 200, where the new athlete will joint the ranks of the preexisting athletes of known skill level. Classification and comparison may thus be completed again to strengthen the system's rules as time moves on and additional athletes are added to the system.

A report generator 210 may take raw data from the classifier and merge it with format data from the reports data store 218. Various pre-existing report formats may be used, and each athlete may be provided with a variety of reports, where the number and detail of the reporting may depend on a level of service purchased by the athlete. For example, basic data from a number of athletes for a particular skill may be pulled from the client data store 216 (along with indicators of the skill level of the athletes), and corresponding data for the current athlete may be placed in line with that other data. The current athlete may thus readily see how he or she stacks up relative to others in skill level, and with respect to the particular drill. For example, an high school athlete may perform at a division II college level for a certain drill and may readily see how they fit with other division II players in that regard, though they may match to junior varsity players with respect to another drill or skill set. Such feedback can be very helpful is letting the athlete determine where they should focus their training.

An athlete can also identify a group with which they would like to be compared. For example, a high school athlete may wish to be compared to all other athletes who have tested on the system in their region or section. Or they may wish to be compared to other athletes on their team. Such identifications of athletes as belonging to certain geographical groups may be used in addition to identifying them as belonging to certain developmental groups.

Also, an athlete can provide information to third parties to permit access to part or all of their testing data. For example, an athlete who is testing at a division II level on certain skills may provide access to a recruiting coach at a division I school to show the coach how the athlete has made great strides in those areas, and thus will be at a division I level by the time they start playing college sports.

Thus, by using system 200, various athletes can obtain both quick and minimal feedback, and longer and more in-depth feedback, on their athletic performance in a convenient manner. The system 200 may provide objective reviews for certain aspects of athletic performance that may then serve as a baseline for more subjective review of the athlete (e.g., where tests do not reflect heart or leadership ability).

Figure 2B:
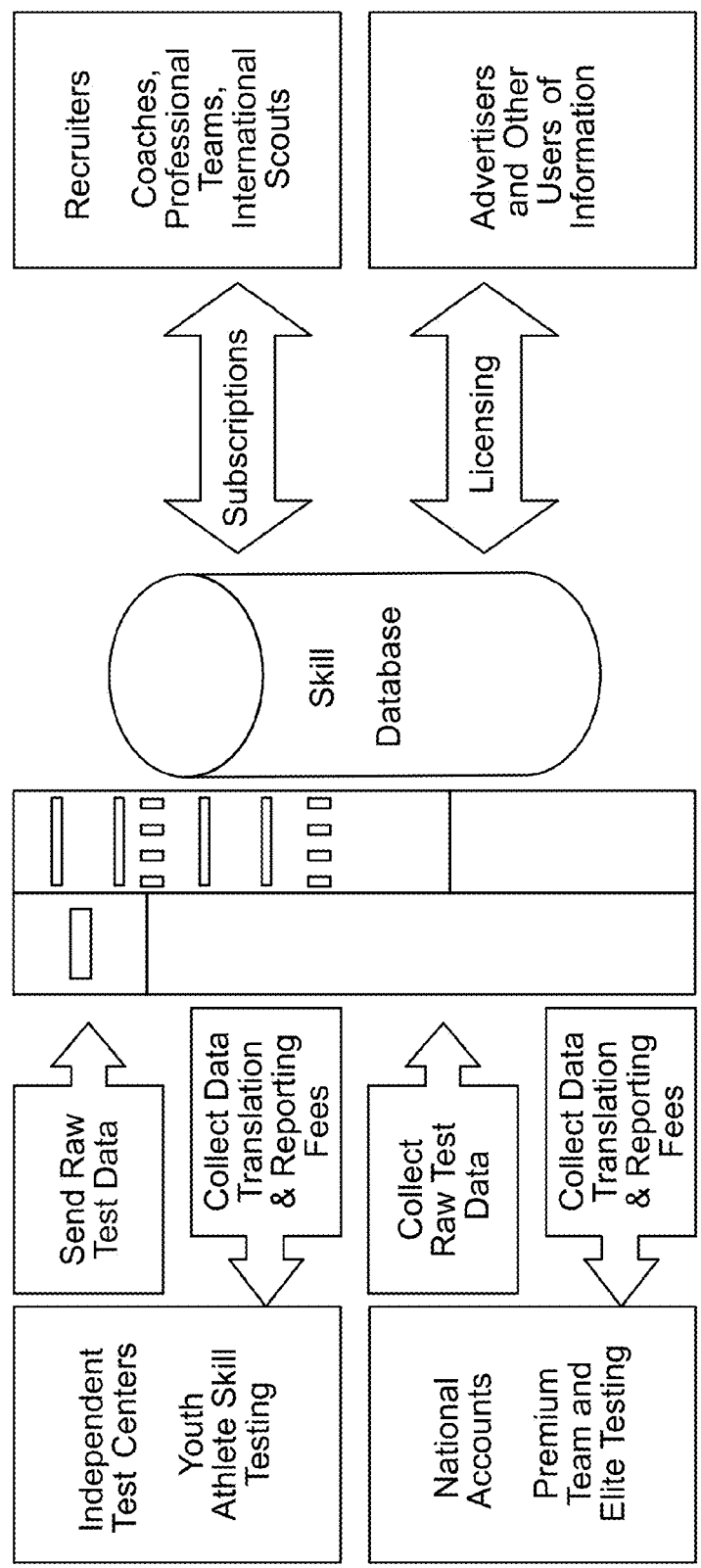
FIG. 2B is a block diagram of a computer-based system for evaluating athletic performance.

FIG. 2B is a block diagram of a computer-based system for evaluating athletic performance. The system in this example is similar to that shown in FIGS. 1 and 2A, but is focused more on the organization of an operational system rather than on the technical provision of data to athletes. The system is focused around a skill database. The skill database stores data of various kinds that reflects performance of a large number of athletes of different skill levels for a number of consistently-applied drill and other activities. The data may reflect, for example, motion data collected from sensors in an athletic device that is separate form an athlete, such as a soccer ball or basketball, and sensors attached to the athlete, such as on a vest or in a shoe or shoes. Certain of the athletes represented in the skills database may have their relative skill level associated with each round of testing, such as according to gross levels (e.g., grade school, high school, college, professional, etc.) or at a more detailed level (e.g., ranked at many levels, and perhaps having different ranks for different drills or skill sets). Other of the athletes may not have an assigned skill level, but may instead be looking to have the system tell them where they stand with respect to the skill levels of other typical users.

Testing and reporting for athletes is shown to the left of the skill database. In this example, two types of operators are identified as having access to the skill database for providing athletes with evaluation data. First, independent test centers may provide testing and evaluation to members of the general public. They may have client systems like those discussed above, to collect the data from athletes such as youth athletes at camps, performance improvement centers, and the like, and may deliver reports and recommendations to the athletes. They may also collect payments from the athletes and remit portions of the payments to an operator of the skill database.

The second type of operator is the national accounts operator. Such operators may provide premium testing services and may be more closely tied to and regulated by the operator of the skill database. Such operators may visit important accounts such as college sports teams, and may conduct mass testing of athletes for such teams. Again, they may provide the raw data for the testing to the operator of the skill database, and may receive report and recommendation data in return. In such situations, the reports may be more detailed, and may also include grouped reporting functionality. In particular, if a team is tested and the testing indicates a pronounced occurrence of a certain weakness in members of the team, the coaching staff or conditioning staff may add drills or exercises to address the weakness on a more global scale, rather than simply for a particular athlete.

The skills database may also be accessed, sometimes for a price, by other organizations that do not collect data on athletes, as shown to the right of the figure. First, recruiters may access data in the skill database to help them make decisions about recruitment. Each athlete may identify, to the system, the schools to which they are applying, and each of the recruiters for such schools may register with the system in a manner that identifies them as being related to their school, and thus gives them access to data for athletes that have identified themselves as being interested in the school. The recruiters may be provided with tools that allow them to see testing scores for various athletes side-by-side, so that they can better compare their prospects.

Athletes may also include ancillary data for such a system, to be reviewed by recruiters. For example, each athlete may be provided with a preformatted home page where they can post information about their academic success (e.g., their grades and volunteer work) and video highlights of their play (or links to video sites that house the highlights). Links may be provided to such pages so that recruiters may obtain a more complete picture of a recruit. In this manner, the system can serve as a national clearinghouse for athletes interested in collegiate opportunities.

As shown in the figure, advertisers or other third parties may be interested in accessing the system. Advertisers, for example, may wish to promote products, such as sports drinks, to user who access the system. In addition, advertisers may wish to identify athletes that identify themselves as using the advertisers' products so as to establish a connection between exceptional performance and the products. In addition, advertisers may wish to review anonymized athletic performance information to determine where in the country certain users are most interested in such testing, so that the advertisers may target their budgets to such areas.

Figure 3A:
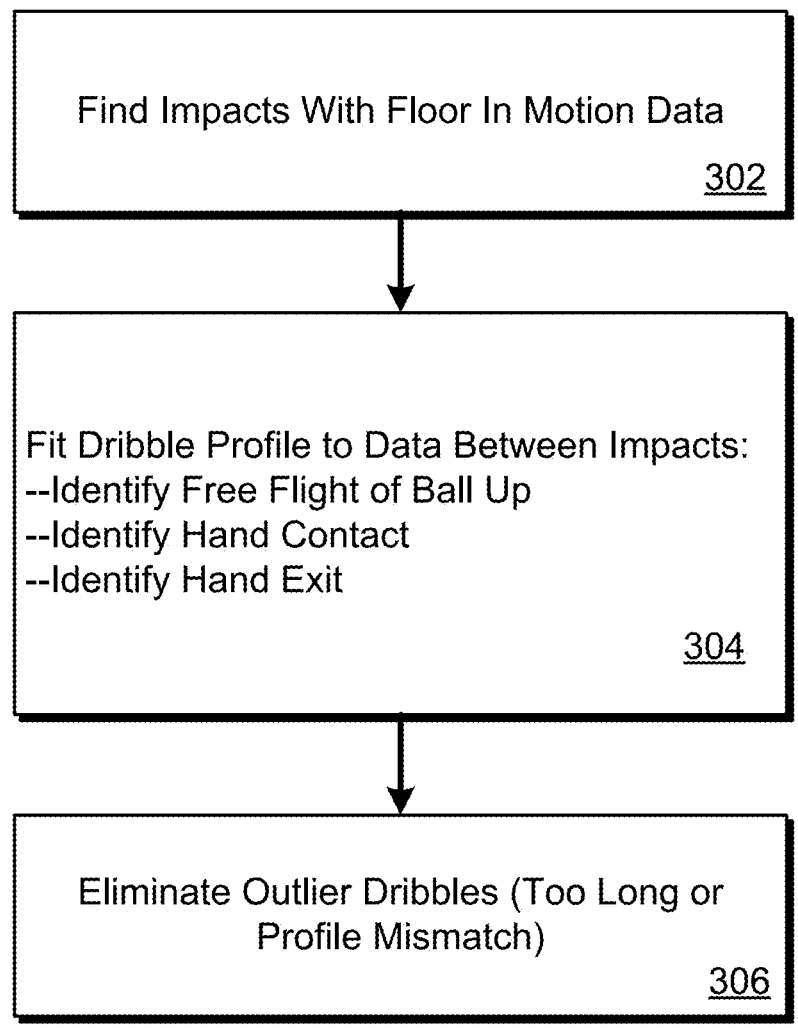
FIGS. 3A and 3B are flow charts of example processes for obtaining motion data relating to an athlete's performance.
Figure 3B:
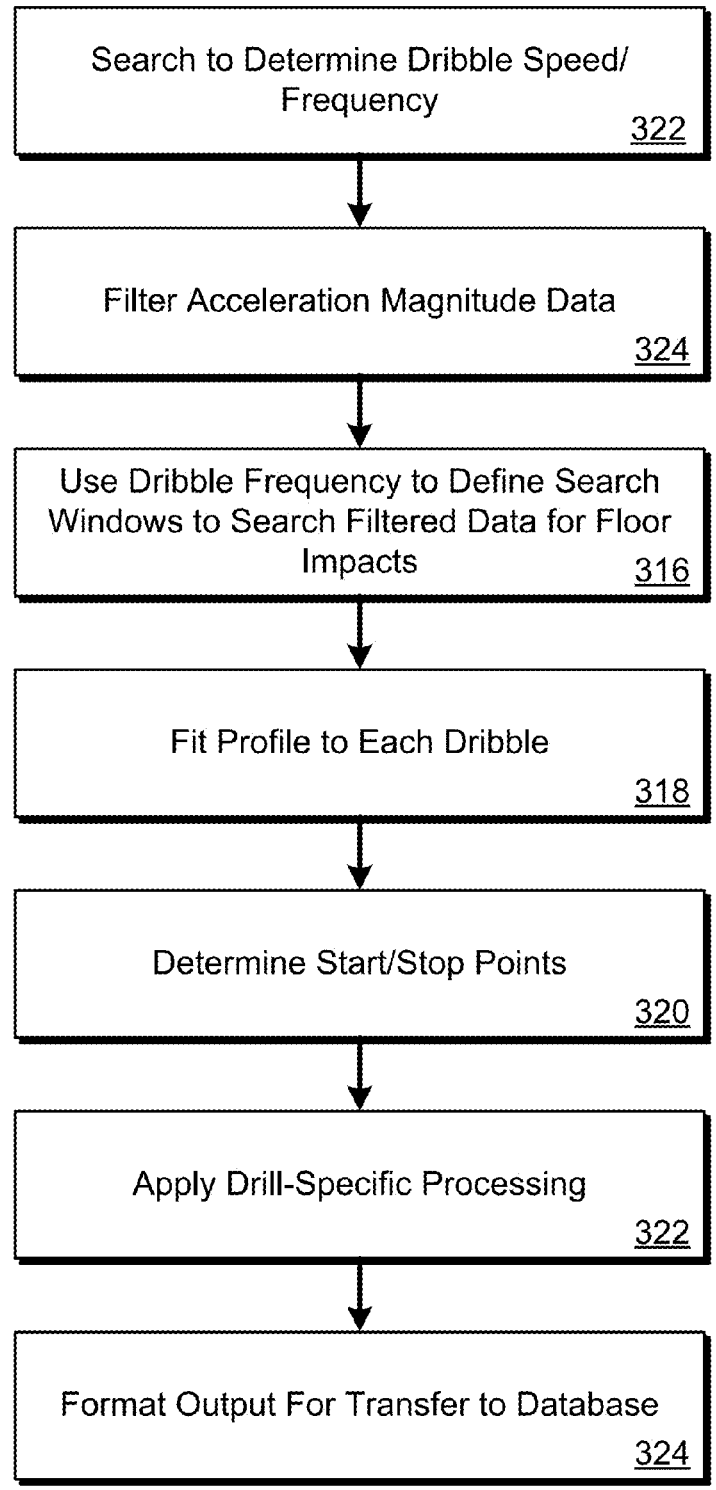

FIGS. 3A and 3B are flow charts of example processes for obtaining motion data relating to an athlete's performance. In general, the process involves identifying particular repeated events in a drill, such as floor contacts by a bouncing ball, and attempting to fit a profile to such events so as to properly characterize an athlete's performance so that it can be compared with characterized performance data for other athletes who performed the same drill.

The process begins at box 302, where floor impacts for a ball are identified in motion data for a drill by an athlete. The impacts can be identified, for example, by identifying sudden changes in an acceleration profile for one or more accelerometers that measured translation of the ball during a drill. At box 304, a dribble profile is fit to the data provided by sensors between impacts with the floor. Such data may show that the user dribbled at a particular frequency, and can also show the manner in which the user received the ball in his or her hand and ejected it from his or her hand. For example, the user may have had a relatively short stroke as part of the dribble, or may have received the ball slowly but pushed it back down to the floor swiftly. Three sub-parts of the dribble cycle can be identified and analyzed in this example: (1) the free flight of the ball between the time it changes direction on the floor to the time it hits the user's hand; (2) the time at which the user's hand contacts the ball; and (3) the time at which the ball exits the hand. Other sub-events in the dribbling cycle may also be the focus of the analysis for athletic traits that are determined to be affected by such sub-events.

At box 306, outlier dribbles are eliminated from the data. For example, a ball may get away from an athlete, so that the athlete misses a cycle of the dribble. Or the athlete might otherwise miss a dribble so that the ball bounces much lower, and the athlete may need to "pound" on the ball to recover the prior dribbling height. Such episodes are removed from the data because they do not represent that athlete's actual regular form.

FIG. 3B shows a process by which various information is filtered out of raw motion data form an athletic device, such as a bouncing basketball, and various parameters that define the motion are discerned. Such parameters or other forms of data may be formatted to permit subsequent comparison between the performance of a first athlete at the drill, and the performance of other athletes at the same drill, so that a relative skill level of the first athlete can be determined.

The process begins at box 322, where motion data is searched to determine a dribble speed or frequency for an athlete's performance of a drill. This action may be used to quickly estimate the dribble speed for a trial. The action may operate on the raw acceleration magnitude signal from a ball, where floor impacts are selected as any acceleration signals above 18.5 g's. Since multiple points above 18.5 g's are likely for each floor impact, a refinement of the original set is made by looking for points that are at least 50 data points apart (0.050 seconds, at the sampling rate used in the example here). The mean and standard deviation of the distance between remaining indexes (time to complete a dribble) are then calculated, and differences beyond 1 standard deviation are ignored, and the dribble speed is estimated as the mean of the remaining indexes, in this particular example.

At box 324, acceleration magnitude data is filtered from the raw data. Such action may be used to reduce the noise in the signal so that the signal can be analyzed and processed more readily. To perform such filtering, the acceleration and angular velocity signals from the motion data are passed through an eighth order butterworth band pass filter with pass band of 0.001 Hz and 15 Hz (where the upper limit could be made to depend on dribble frequency). This filter is very similar to a low pass filter at 15 Hz.

Although the particular example here has been described as using both spin data and translational data for a ball, determinations may also be made regarding when an athlete loses or regains control by using only one type of data. For example, acceleration data may be used, without spin data, by determining the sequence of ball impacts and hand impacts. Floor impacts generate more force than a hand impact, and control of the object is determined by a sequence that always includes an alternating floor-hand-floor-hand sequence. If the process cannot locate a hand impact between two floor impacts, it can indicate a loss of control of the ball. Thus, a predetermined minimum force measurement (which can be determined from acceleration data) can be defined for a hand impact, and a pre-determined minimum force measurement can be defined for a floor impact. If the patterns reveal two floor impacts in succession, loss of control can be determined. If the patterns reveal a pre-determined number of floor-hand-floor-hand patterns, control has been regained. In this fashion, a determination of ball control and lack of control can be made, and thus all other calculations about the ball's movement can be counted within the periods of the ball being in control.

Figure 13A:
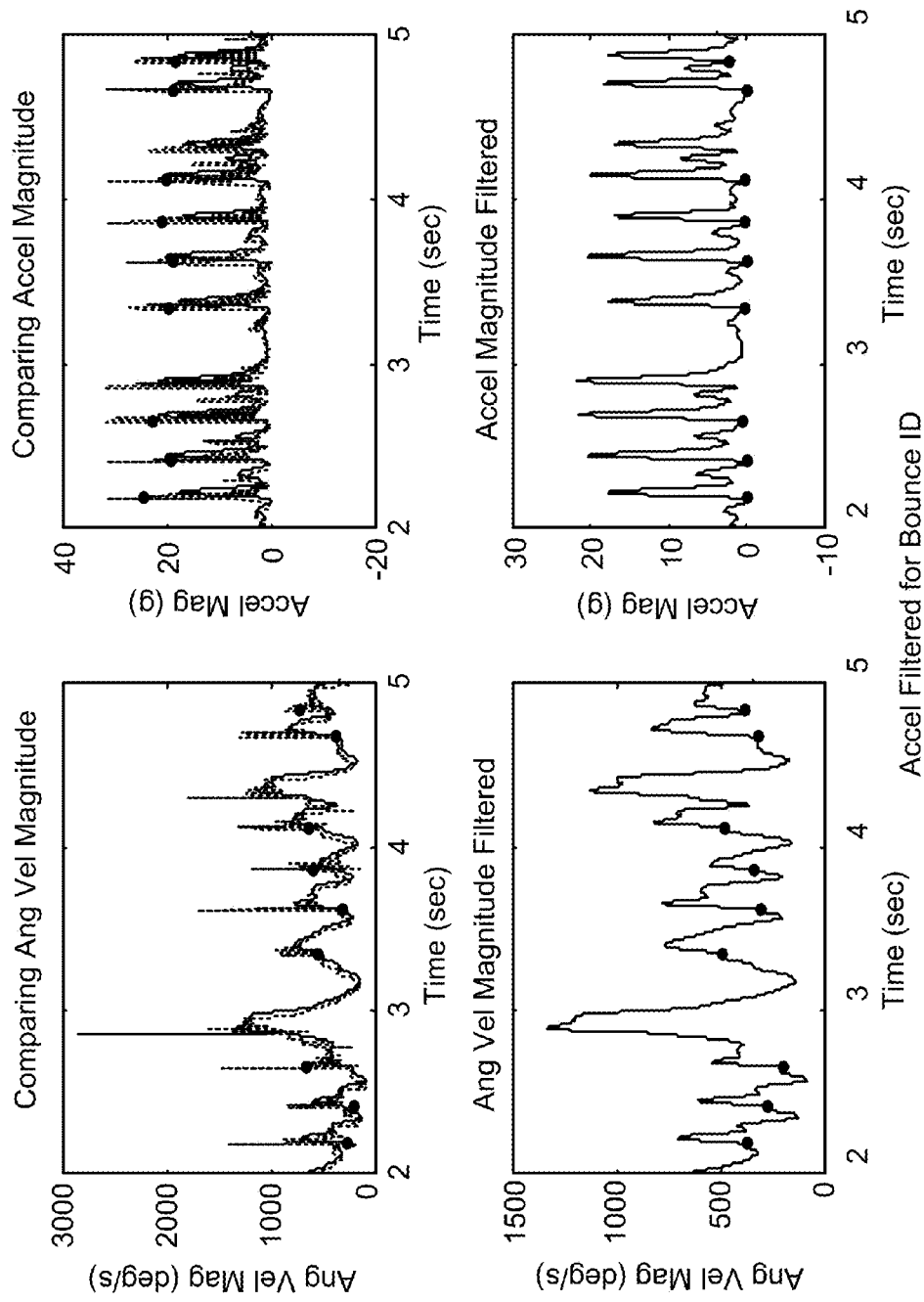
FIGS. 13A-13K are graphs that show how raw motion data may be reduced and filtered into a form suitable for analysis of particular basketball motion, such as dribbling.
Figure 13B:
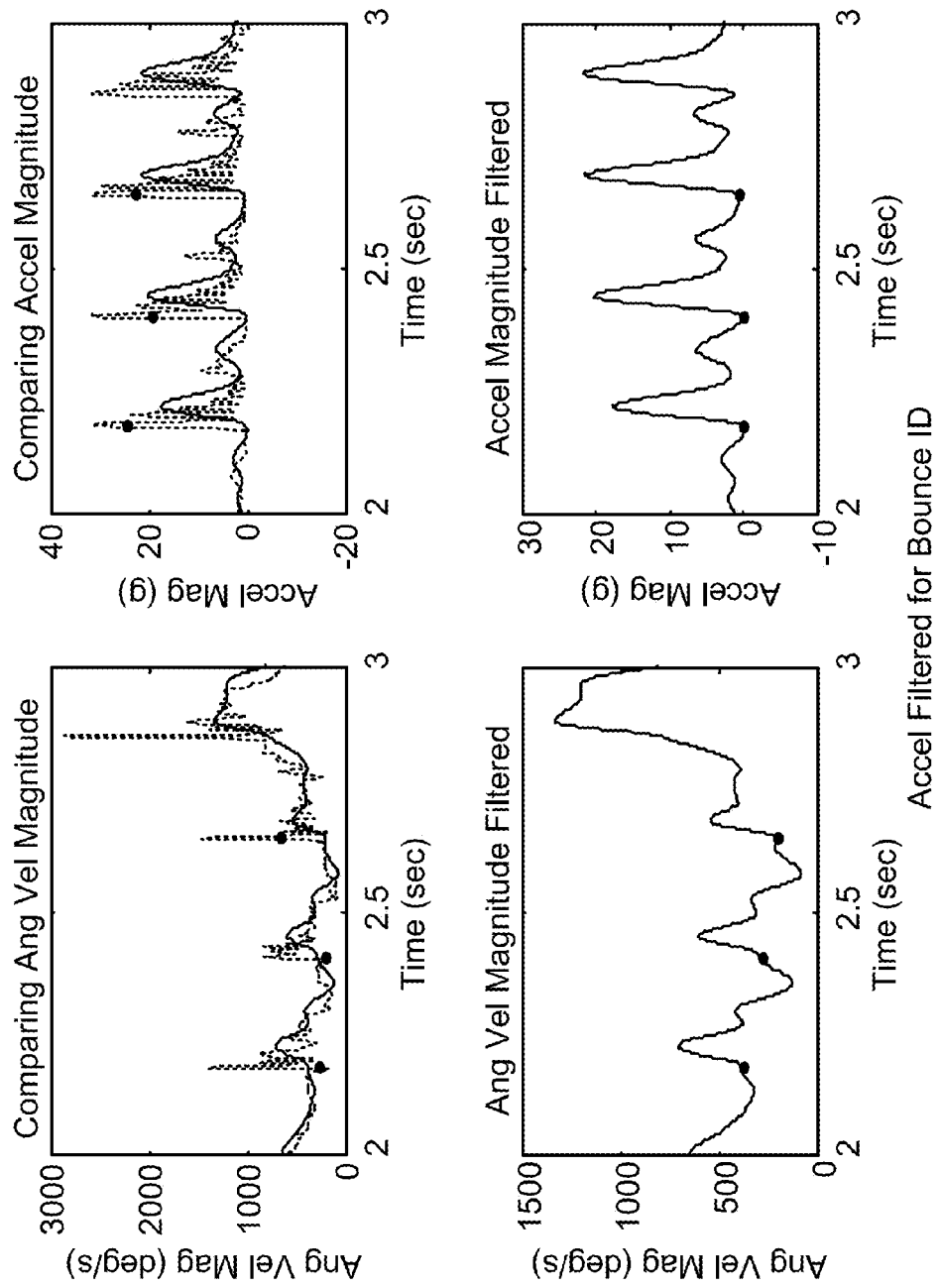

FIGS. 13A-13K are graphs that show how raw motion data may be reduced and filtered into a form suitable for analysis of particular basketball motion, such as dribbling. FIG. 13A shows two subsets of data taken from a single trial of a first athlete dribbling a basketball in a figure eight pattern, where the athlete is a Division II level college basketball player. The left graphs show the level of angular velocity, while the right graphs show the level of translational acceleration of the basketball. The upper graphs shows both the filtered and unfiltered signals, while the lower graphs simply show the filtered signal. FIG. 13B shows the same information, but zoomed into a particular part of the data from FIG. 13A. Green dots have been superimposed over the signals (though they are most visible in the lower graphs), and they represent points that the search in box 322 identified as being floor impacts. One can see that the noise of the signal has been reduced from the upper graph to the lower graph by the filtering. Now for each dribble there is a single peak for floor impact and in most cases a smaller peak corresponding to impact with the athlete's hand.

At box 316, the process uses the dribble frequency to define search windows to be passed over the signal to search for floor impacts. The search windows are used to search through the smoothed acceleration signal and identify the floor impacts. The process searches for a next dribble based on the estimated dribble speed from box 322. At first, the coarse estimated dribble speed is assigned to be an assumed absolute dribble speed, and an initial relative dribble speed. A threshold limit of a certain number of g forces is set for the search, which may be triggered by some hand impacts, but which is designed to catch all floor impact peaks. The next peak search looks at a window that spans no more than a certain time interval as determined by a calculation based partly on the average dribble frequency of that drill for that player. The relative dribble frequency is updated to be the dribble frequency of the last 4 good bounces. Such adjustment addresses actions by an athlete that involve speeding up or slowing down, so that the most recent information is used.

The data in the time window can have three outcomes: (1) A local maximum is found above the minimum g force threshold (success in finding next bounce); (2) no points above the minimum g force threshold are found; and (3) a point above a minimum defined g forces is found but it is on the edge of the window.

If the search concludes with outcome (1), the point is registered as the location of the next bounce. If the search concludes with outcome (2) (no point above the minimum g force threshold's) the process searches forward (by moving the timing window) looking for the next peak at or above the minimum force threshold. When the outcome is (2), the process also resets the counter of good bounces, which means that a new relative dribble speed will not be calculated until another 4 bounces are identified in a row.

If the search concludes with outcome (3), the process searches backward and forward for the next peaks, regardless of their magnitude. The process then checks to see if either of the nearest peaks are above minimum defined g forces. If only one is above the minimum defined g forces then that one is selected as the next bounce. If both are above the minimum defined g forces, the one closer to the relative dribble frequency is selected. Outcome (3) may produce a result in which a window can register a point that is above the minimum defined g forces, but where that point is not at the apex of the signal, and thus does not represent a bounce peak.

Figure 13C:
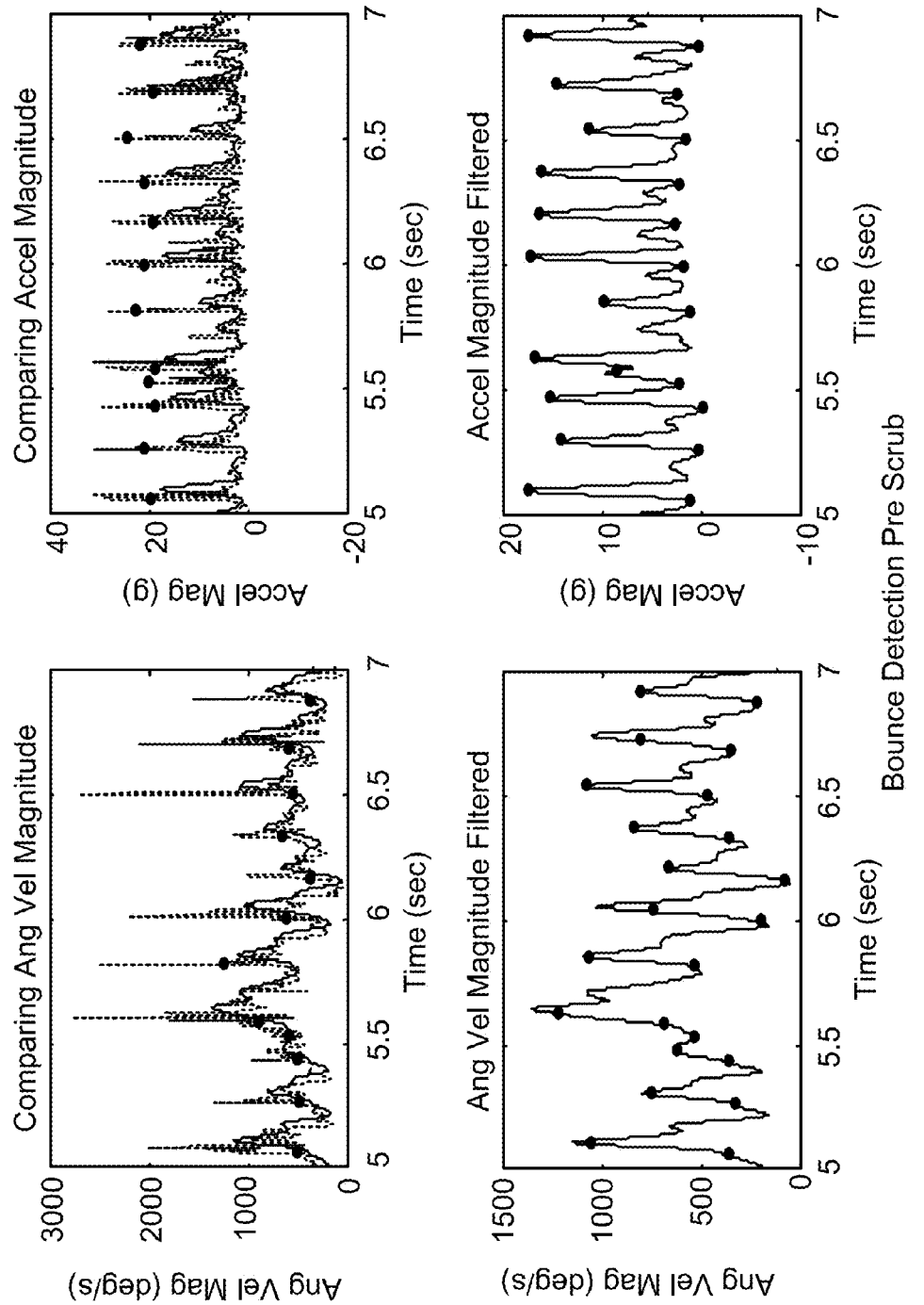

FIG. 13C shows graphs of such a searching process, using data from the same athlete that drilled for FIGS. 13A and 13B, and again on the athlete's figure eight data. The upper graphs show unfiltered data, while the lower graphs show only the filtered data. Dots are superimposed over the signal to identify points that have been located via the process in box 316. The original dots from the coarse peak identification (which are mostly located at points below the new dots) are also still shown. Notice in the figure that, between 5.5 and 7, there are three previous dots, as the hand contact was improperly identified as a floor impact, and only two new marked dots in this same period.

Figure 13D:
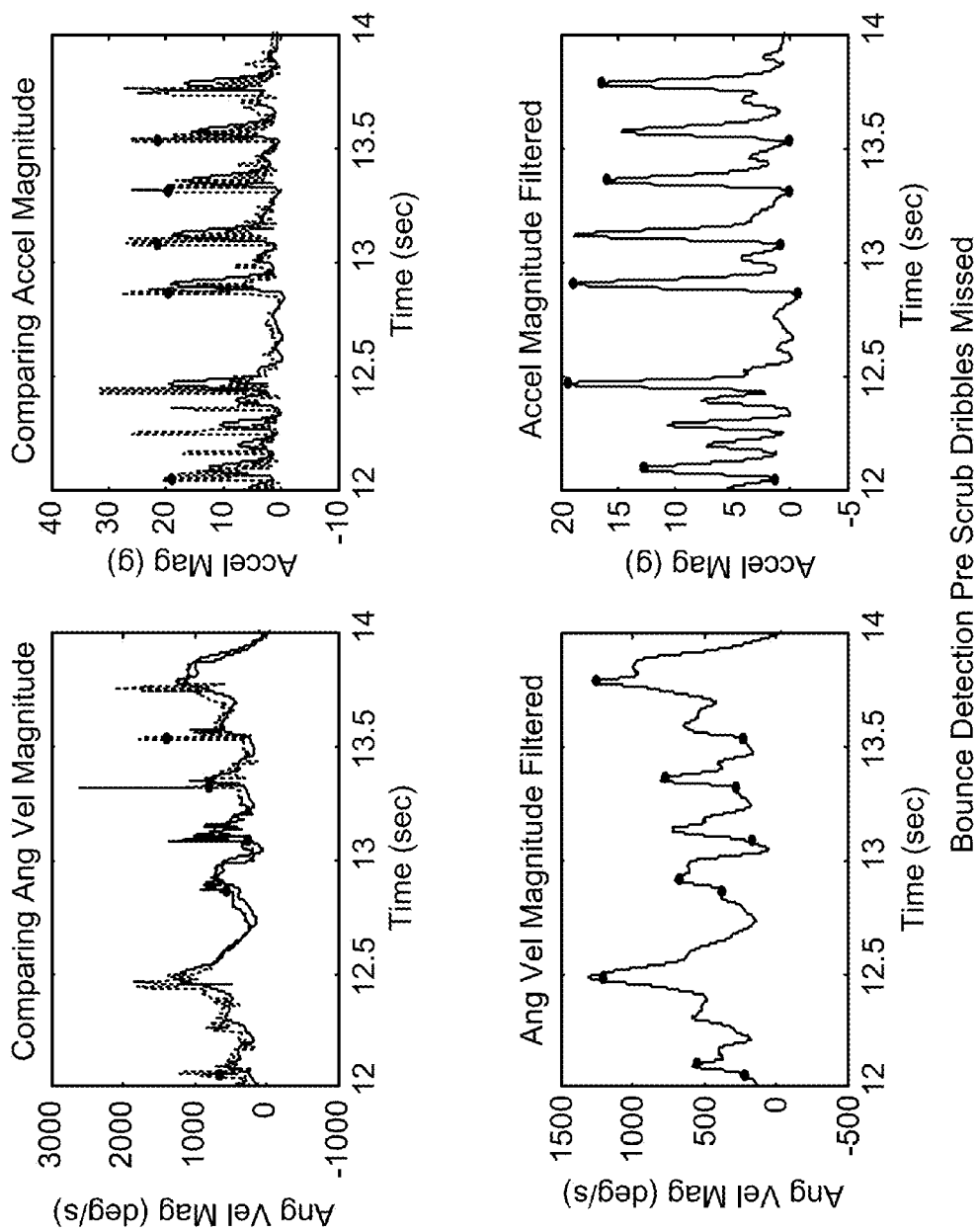

FIG. 13D shows a failure mode for the action at box 316, where the process locks onto a dribble speed that is double the actual dribble speed (which may occur when more than one type of dribble is being performed in a drill). As shown by the dots in the figure, every other dribble has been missed.

As an additional action, the identified points may be further processed in an attempt to identify hand contacts that were erroneously classified as floor contacts. In one example, the process identifies floor impacts below 16 g's. It then considers the next three peaks. If the distances from the middle peak to each of the previous and later peaks are less than a defined level of dribble speed, and if doing away with the middle peak would be within a defined range % of the dribble speed, then the process removes the middle peak.

Figure 13E:
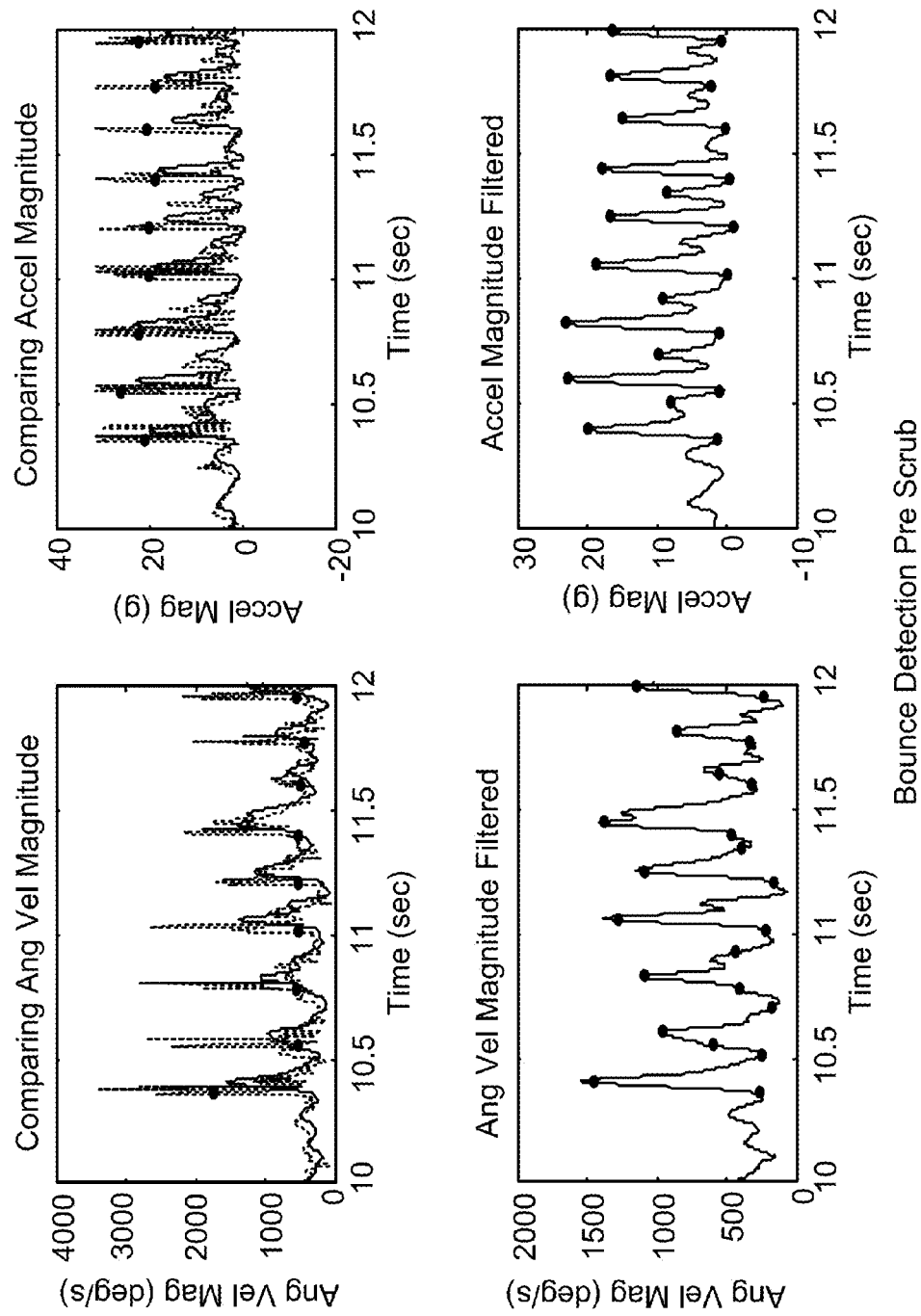
Figure 13F:
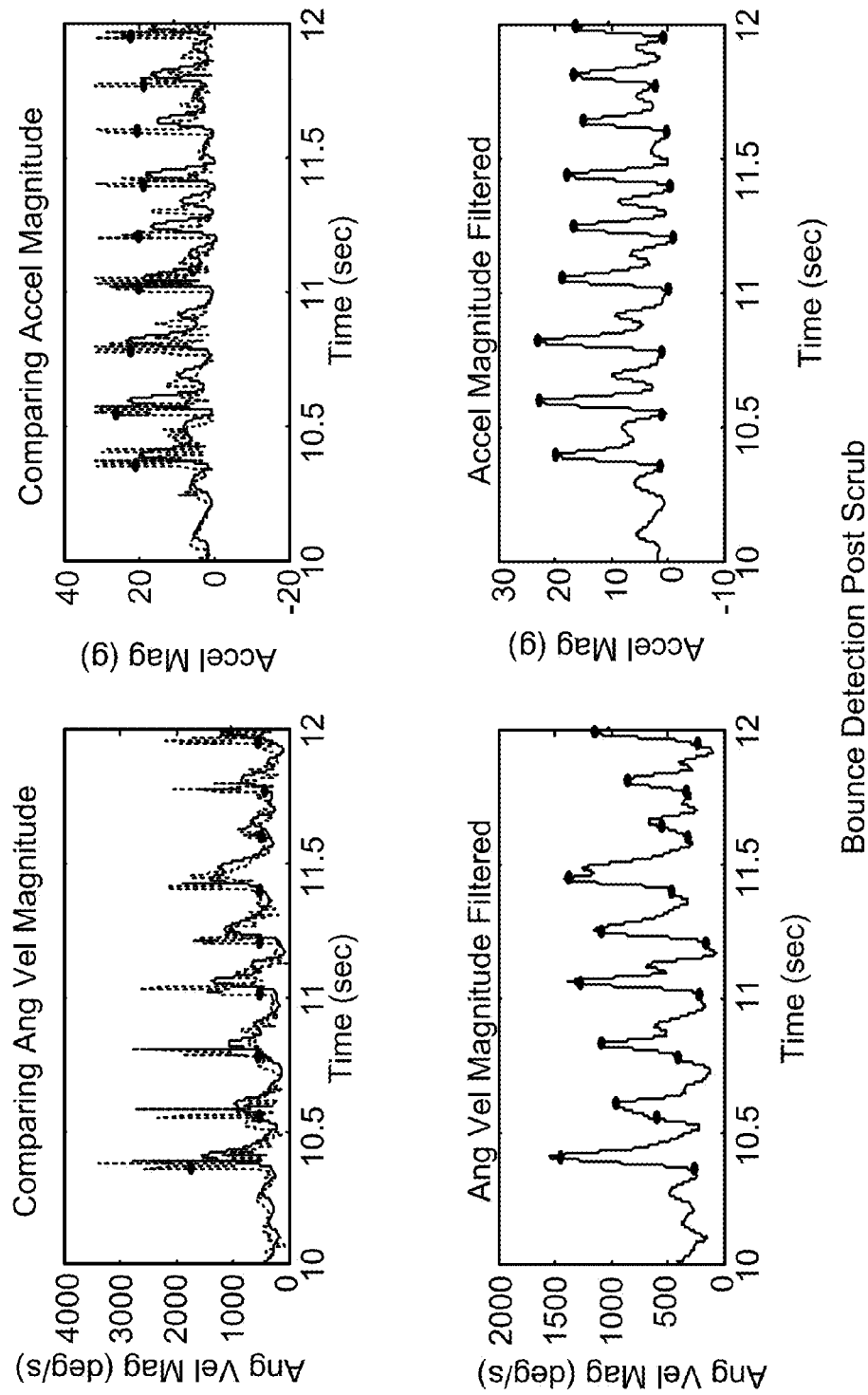

The results are shown in FIGS. 13E and 13F, for data from a drill performed by a second athlete who is different than the first athlete. Notice that there is a significant time difference between the dots from the original coarse pass and the corresponding new dots. This is due to a time shift cause by filtering. Because it may be preferable to return closer to the original signal, a search can be executed for each new dot backward until a peak is found in the raw data. Upon completion of such an operation, the process may assume that that only peaks associated with floor impacts have been tagged, and no floor impacts have been missed.

The process then proceeds to box 318, where a profile is fit to each dribble. By this point, all the floor impact peaks (and only floor impacts) have been marked. The process now attempts to fit an expected profile to the data between floor impacts. The first step is to filter the data, such as by using a moving average filter. The filter can use an adjustable number of points 'X' (which could be tied to dribble speed) and replaces the current point by the average of the 'X' previous points and 'X' following points. This has the effect of low pass filtering the data with minimal phase shift. The process then moves to the center of the data window and searches the acceleration signal left and right for a peak above 3.5 g's. If no peaks are found, it lowers the threshold by 0.5 g's until the peak threshold falls below 1.2, at which point the process eliminates the current window as a valid dribble.

If peaks are found (where two forward and two backward are the search goal), the width of each peak is calculated. The width is defined, in this example approach, as the time distance when the peak has lost 120% of its max value (or has fallen below 1.3 g's). For a peak to be selected in this example, it needs to have a full width of at least 15 data points, and each half width (distance from peak to right or left edge) of 15/2. If multiple peaks meet these criteria, then the one closest to the midpoint of the dribble is selected. If no peaks meet the criteria, then the current window is eliminated from the set of valid dribbles.

Once a hand contact acceleration peak is identified, the process determines when the hand first touched the ball. As a starting point, the process searches back in time to find the nearest minimum point to the hand contact peak. This minimum is marked as the dots on the signal graphs in FIGS. 13G and 13H.

The process then analyzes the spin data from the sporting device motion data. The spin data should normally be oscillating about a free flight spin rate. This free flight period will generally be a period of constant spin because no external torques are being applied to the ball (ignoring air drag), and therefore angular momentum should be conserved. The process then searches around the acceleration minimum (shown by the point identified in the prior paragraph) for an oscillatory signal.

To prevent unintended small oscillations from triggering the process, the process is only triggered in this example if the free flight spin rate is 150-350 deg/sec (a choice can be made depending on dribble frequency) and if spin drop from free flight to the next spin minimum is at least 100 deg/s. Also, the spin rate needs to decay when the player's hand touches the ball, so a drop in spin rate should be observable in every valid dribble.

A search for oscillation in the spin data is performed as follows, and is performed for each dribble. A search back from the dot identified above is first made to find a peak that is at a minimum pre-defined threshold, in this case 85% of the free flight spin rate. The search may be conducted by finding the next local max, and, if that max is not large enough, the process moves back to the next local max. This movement backward may continue until a valid peak is found or the search runs out of data (in which case, the last invalid max is preserved for the next step).

Figure 13G:
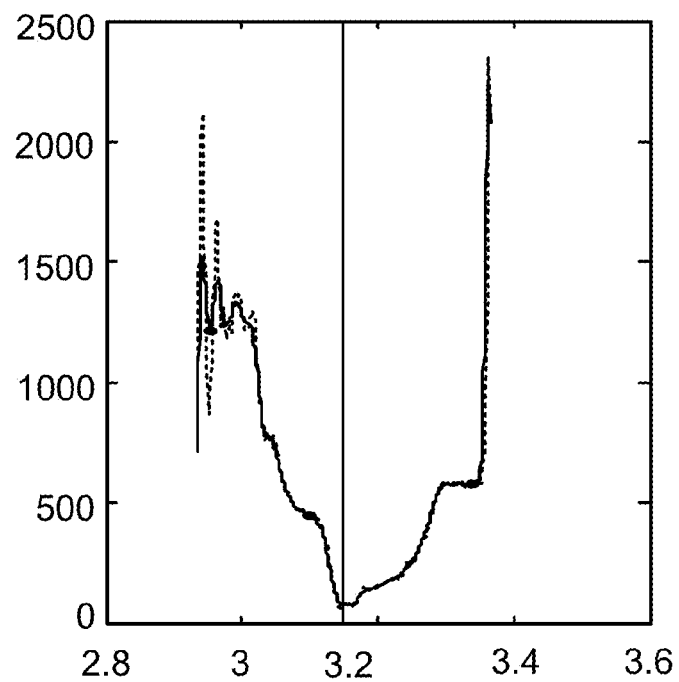
Figure 13G:
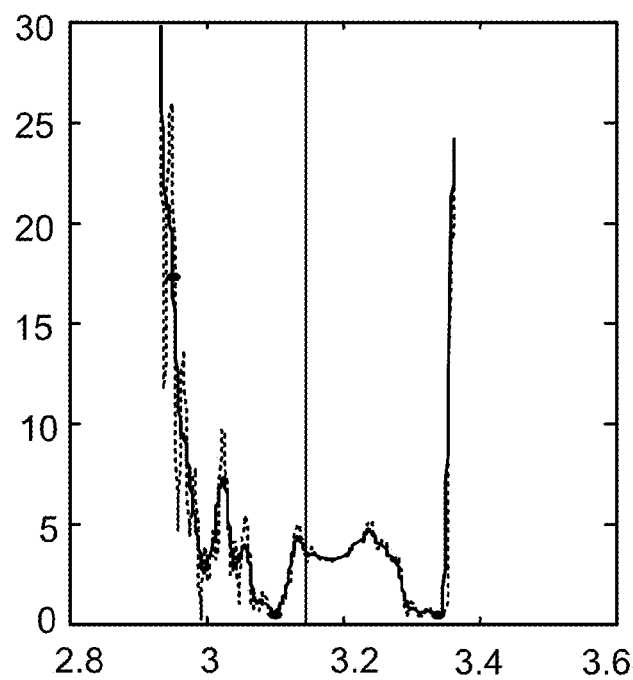
Figure 13H:
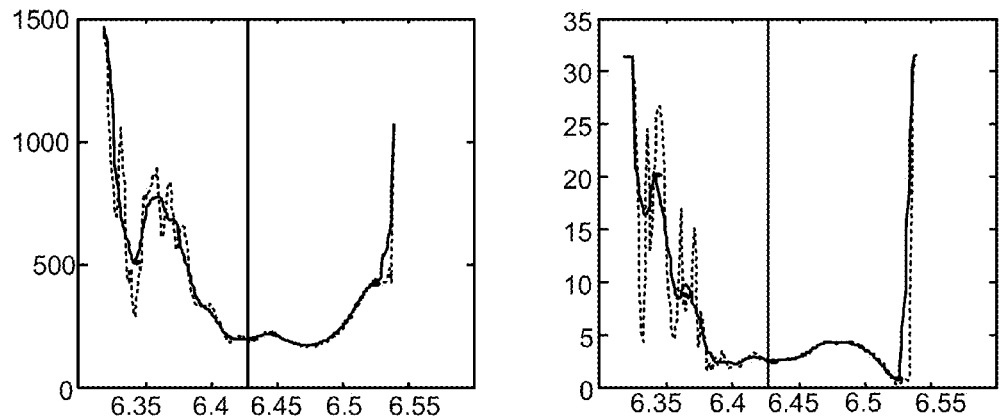
Figure 13I:
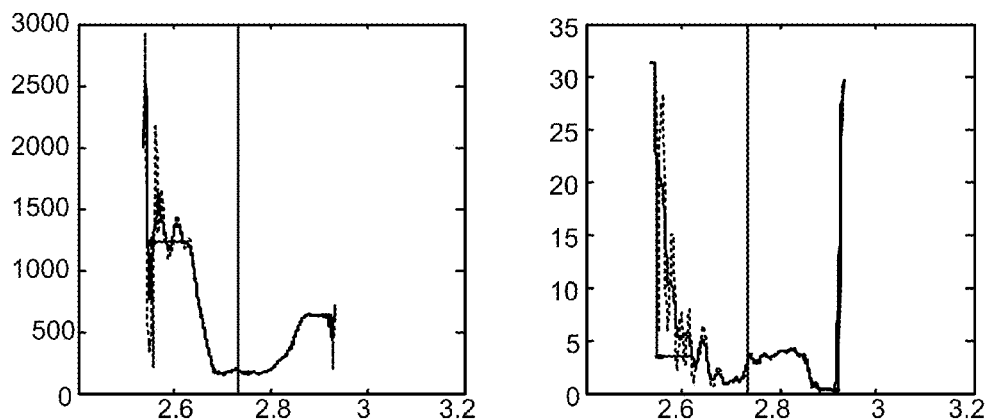
Figure 13J:
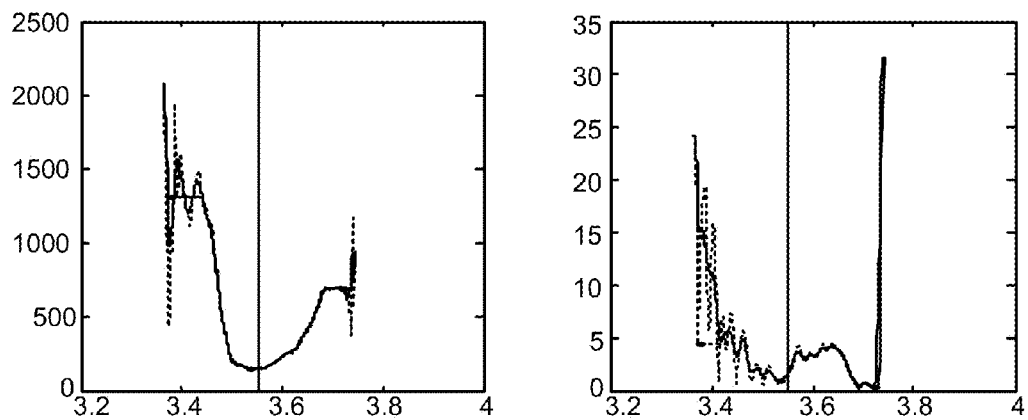

A second search looks for a local spin maximum moving forward from the dot to the acceleration hand peak. Because the forward search will frequently not find an actual max, and will thus return one of the end points, a check is made to determine if that point is truly a max by checking the local slope of the line. The example in FIG. 13G shows such a feature.

The appropriate maximum may be selected by first checking whether the maximum backwards value less the value at the dot discussed above is >100 (which checks the spin drop), and the maximum backwards spin is close to the window (i.e., no more than halfway to the edge of a window). If such a check is true, the point is used as the free flight maximum spin. If neither test is met, the constraints are relaxed if the maximum backward spin less the minimum spin for the trial is >100 or if the hand acceleration increase (from dot above to the maximum acceleration) is at least 4 g's. If the constraint is met, then the point is accepted as the maximum free flight spin. Now with a maximum free flight oscillation or spin identified, the previous minimum is sought. If no local minimum is found, then a feature of time in hand does not exist, and the bounce is not used.

If a minimum free flight oscillation is found, the free flight spin rate is set to the average of the maximum and minimum rates ((MAX+MIN)/2). The process then marks the first time that this spin rate occurs in the window, and also marks the last time this spin rate occurs before the hand acceleration peak. This section of data can then be assigned a constant value. A determination may then be made of the times at which the ball has left the athlete's hand by finding, for each dribble, the first point after the peak of the hand contact acceleration where the acceleration reaches the level of the rightmost dot from above (i.e., the first local minimum before the floor impact). The process then repeats for the remaining dribbles.

Figure 13K:
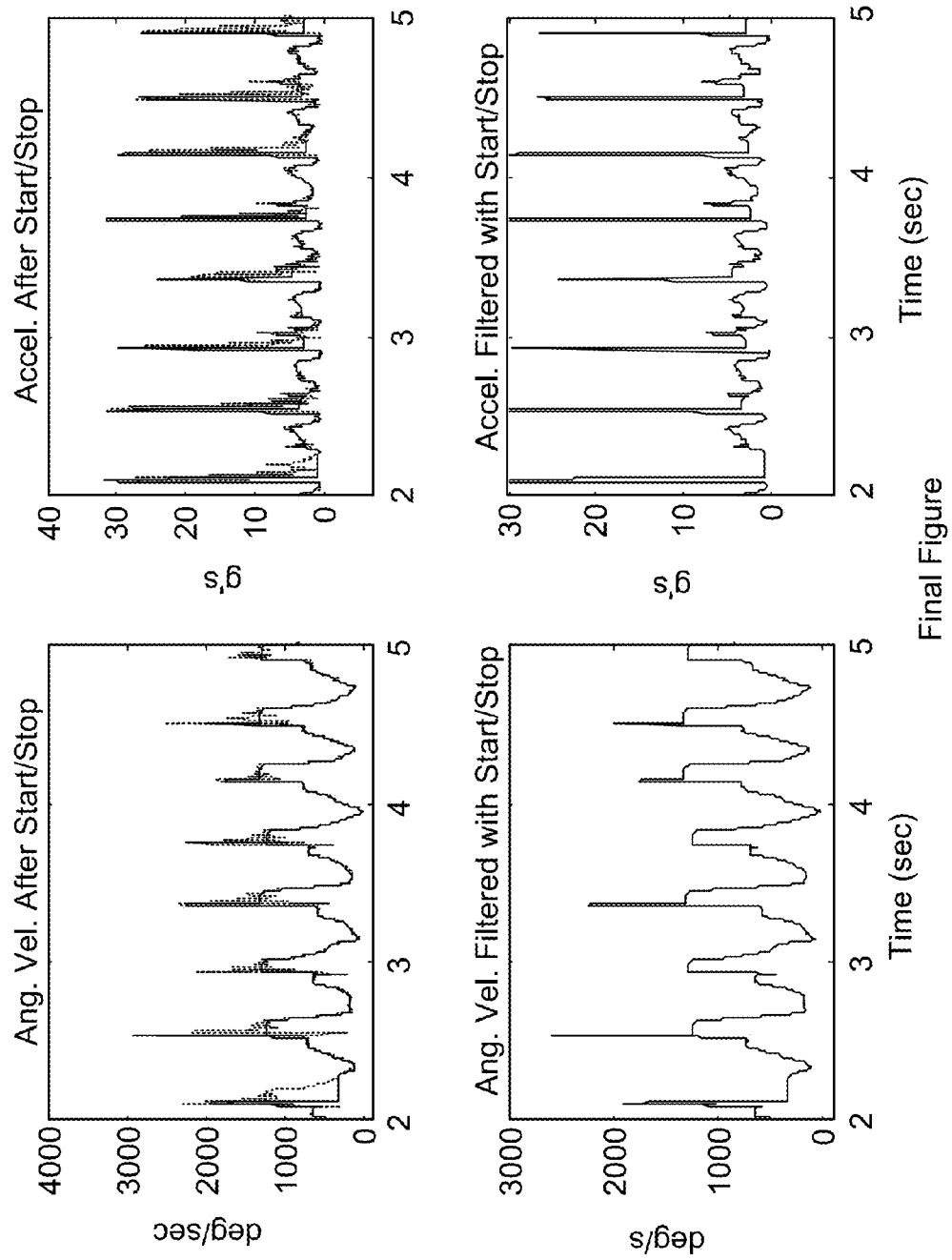

At this point, each dribble has been filtered and the free flight period after the last floor impact has been identified in terms of duration and spin rate. FIG. 13K shows a section of controlled dribbles that have been filtered and have the expected profile fit to them, for the first athlete above. Again the left graphs represent angular velocity, while the right graphs represent translation acceleration. Also, the top graphs show both filtered and unfiltered signals, whereas the lower graphs show only filtered signals.

Returning to the process of FIG. 3B, at box 320, start and stop points for a drill are determined. Some start/stop points have already been identified by the bounce processing process, although nearly all data between impacts is used. Portions of the signal in which the spin rate is constant between successive floor impacts can indicate a ball spinning in motion in which no forces are acting on the object. Also, the process may identify gaps that are 2.5 times greater that dribble frequency (other determinants may also be employed) and eliminates data in those gaps because those signals may indicate an impact on the sensor causing a signal that is abnormal. The start/stops are then combined with any start/stops that were earlier identified by the prior portion of the process, and the process then checks to make sure there are at least three good dribbles between start/stops. If there are fewer than three good dribbles between start/stops, such dribbles are eliminated. Then first and last bounces are identified and the beginning and end data is trimmed.

At box 322, the process applies drill-specific processing to the data. Drill-specific processing may be a sub-process that recognizes that each drill may have certain attributes that make it unique from other drills. For example, a figure-eight dribbling drill in basketball requires that the athlete dribble around one leg, crossing the ball between the legs to the opposite hand, then repeating a dribble around the other leg. The crossover dribble may have a unique dribble signature that is different from the other dribbles and unique to this drill. The drill specific processing can be designed to recognize this pattern for this particular drill, which allows the scoring sub-process to count these occurrences as part of its analysis. These occurrences may not appear in another drill. For example, in a drill that requires the player to dribble behind the back from hand to hand, there is no crossover dribble signature to measure, and thus the drill-specific processing to score various measurement points may differ.

At box 324, the output is formatted for transfer to a database, where it can be accessed in the future for purposes of comparison to data of other athletes or comparison to data form drills performed by the same athlete in the future (i.e., so as to show progress by the athlete). When output is reformatted, various aspects of raw data (e.g., acceleration forces) can be averaged, or standard deviations can be identified of a plurality of bounces. These calculations are tabulated, and used in a pre-determined mathematical formula to create an output that can be understood by those who are may not be proficient at math. In this manner, for example, tabular data that can be easily searched and compared, may be produced from data that represents the "shape" of the motion of the sporting device.

Figure 3C:
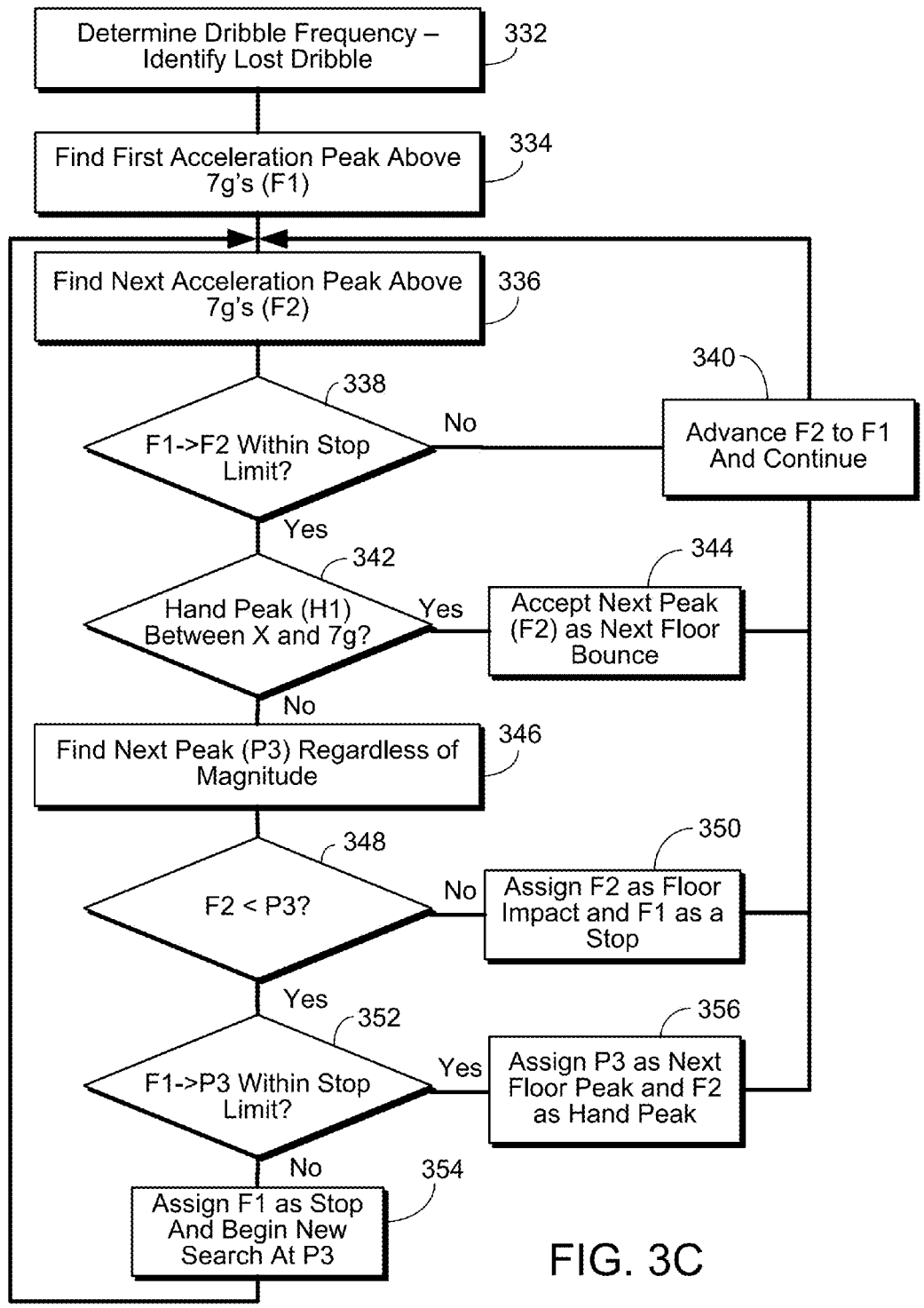
FIG. 3C is a flow chart for identifying particular events during a drill that involves bouncing a ball.

FIG. 3C is a flow chart for identifying particular events during a drill that involves bouncing a ball. In general, the process is directed toward recognizing a pattern of start/stop points in the motion data of a ball that has undergone a drill controlled by an athlete. The process begins at box 332, where a dribble frequency is determined, and also abnormal dribbles are identified, as by increased lengths in dribble frequency that are above a stop limit that is defined as a certain level above the average dribble frequency. At boxes 334 and 336, the process finds acceleration peaks in the data that are above minimum defined g forces. The process works on, and moves across, pairs of such points and the data between them, where the first point in a pair is designated F1 and the second is designated F2.

At box 338, the process determines whether the time between F1 and F2 is within a predetermined stop limit, which may be a factor of the dribble frequency. If it is not, then the process pushes the point of F2 back into F1 moves on to identify a next F2. If it is, then at box 342, the process determines whether there is a hand peak (H1) with a magnitude above a predetermined value of X, but less than a minimum defined g force, herein shown as 1.2 g's. If there is, then the next peak (F2) is accepted as the next floor bounce, and the prior F2 is transitioned to F1. If there is not, the process finds the next peak (P3), which is found independent of its magnitude.

At box 348, the process determines if the current F2 is less than P3. If it is not, then F2 is assigned as a floor impact and F1 is determined to be a stop. The process then indexes forward a position and repeats. If it is, then the process determines at box 352 whether the time between F1 and P3 is within a predetermined stop limit. If it is, then P3 is assigned as the next peak for a floor bounce, and F2 is assigned as a hand peak (and the process indexes forward to the next point). If it is not, then F1 is assigned as a stop point, and a new search is begun starting at P3.

Particular Description of Basketball Shooting Motion

The following section describes measurements that may be taken to characterize the motion involved in shooting a basket with a basketball using, for example, inertial sensors in the basketball.

The following list of shooting metrics is presented as initial concepts of the types of measurements that are capable.

Release time—the time from when the passed ball initially contacts the shooter to the time when the ball is released at the end of the shot motion Shot Velocity—the vector quantity can be calculated throughout the shot process with particular interest in the velocity at shot release Shot Plane—a plane of particular interest that contains a vertical unit vector and the shot velocity vector calculated at the instant of shot release.

Shot Arc—the metric describes the path the ball traveled on the way to the basket. The shot arc can be calculated from the velocity vector at shot release, by calculating the inverse tangent of the ratio of the vertical velocity component compared to the horizontal velocity component.

Spin Rate—the total spin rate of the ball at shot release. This metric would be reported as degrees per second or revolutions per minute (RPM)

Spin Axis—The body fixed axis of the ball about which the ball is spinning at shot release.

Angular Velocity—this vector can be decomposed into components about axes of importance to shooting. One important set of orthogonal axes which are important to shooting is [backspin, sidespin, and rifle spin]. Being able to determine what percentage of the total spin rate can be decomposed onto each of these directions is critical to developing proper shooting technique.

Shot time—the time from when the shot is release till it contacts the basket.

Shot distance—horizontal distance from shot release point to the basket. This measurement is what would be observed from an overhead view of the shot. This metric is derived from shot velocity and shot time.

Figure 4A:
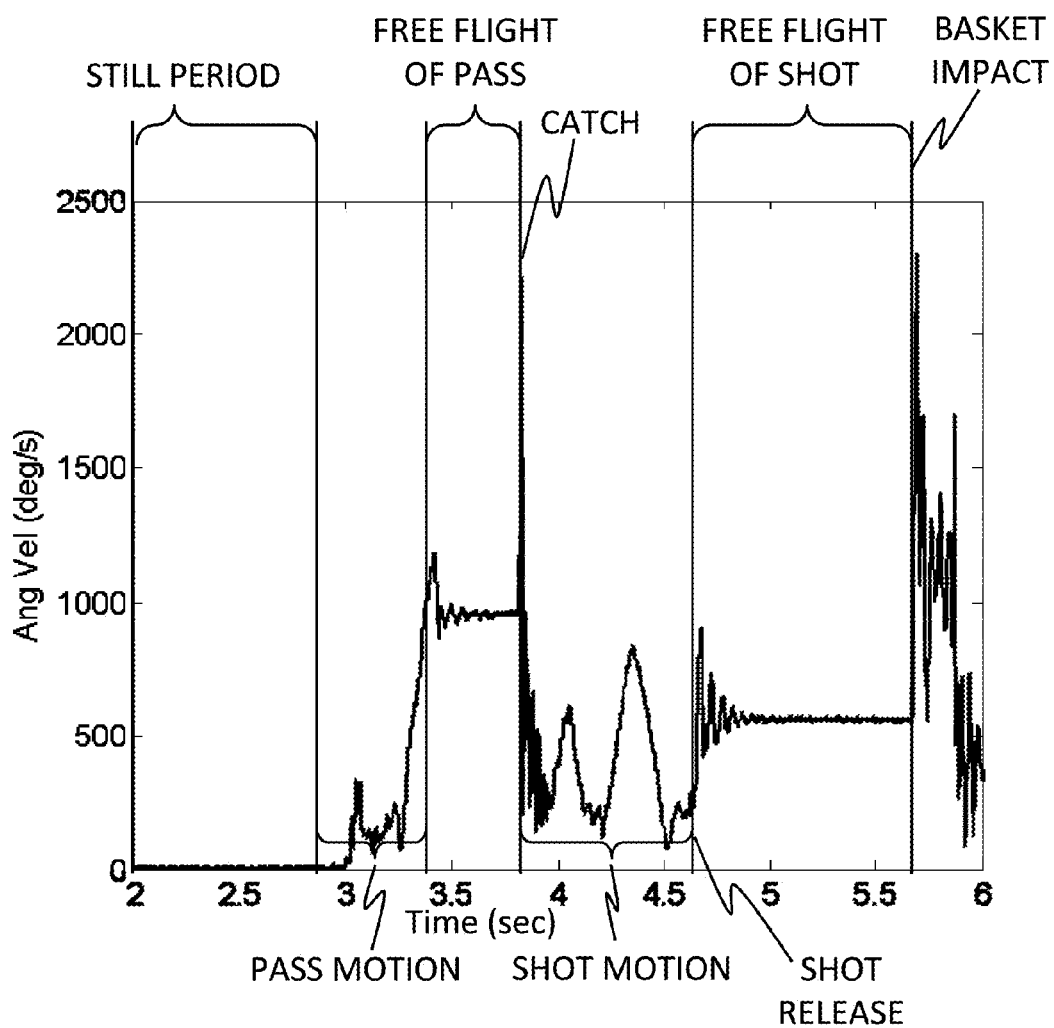
FIGS. 4A-4B show sample motion data from basketball shots taken after a pass.
Figure 4B:
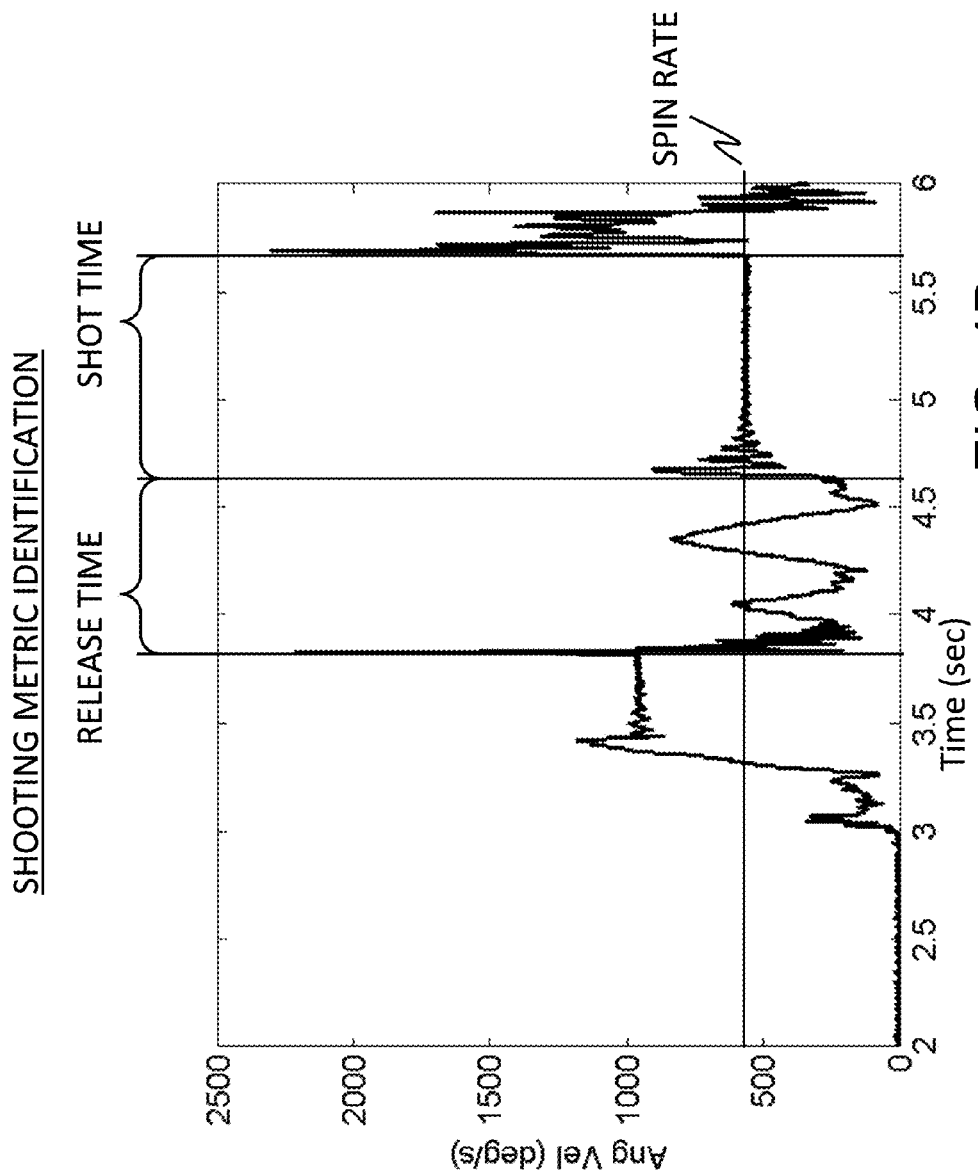

FIGS. 4A-4B show sample motion data from basketball shots taken after a pass. FIG. 4A shows sample data of a shot with annotation of the various phases of a shot. The still period is the period of time where the ball is sitting still before the pass/shot sequence begins. The pass motion is the motion associated with the ball being picked up and thrown to the shooter. Once the pass is released the ball will travel through the air and the physics of this travel can be approximated as torque free motion. The catch occurs when the ball arrives at the shooter. The motion from the instant the shooter catches the ball till the shooter releases the shot is defined as the shot motion. When the shooter releases the ball it enters another free flight motion phase identified as the free flight of the shot. The free flight period, and the shot, ends when the ball impacts the basket.

As shown in FIG. 4B, from the raw data, some of the proposed shooting metrics can be directly identified. The release time can clearly be distinguished as the period of time between the end of the pass free flight period and the beginning of the shot free flight period. The shot time is equivalent to the shot free flight period. The spin rate is the magnitude of the angular velocity vector during the shot free flight period.

Figure 5B:
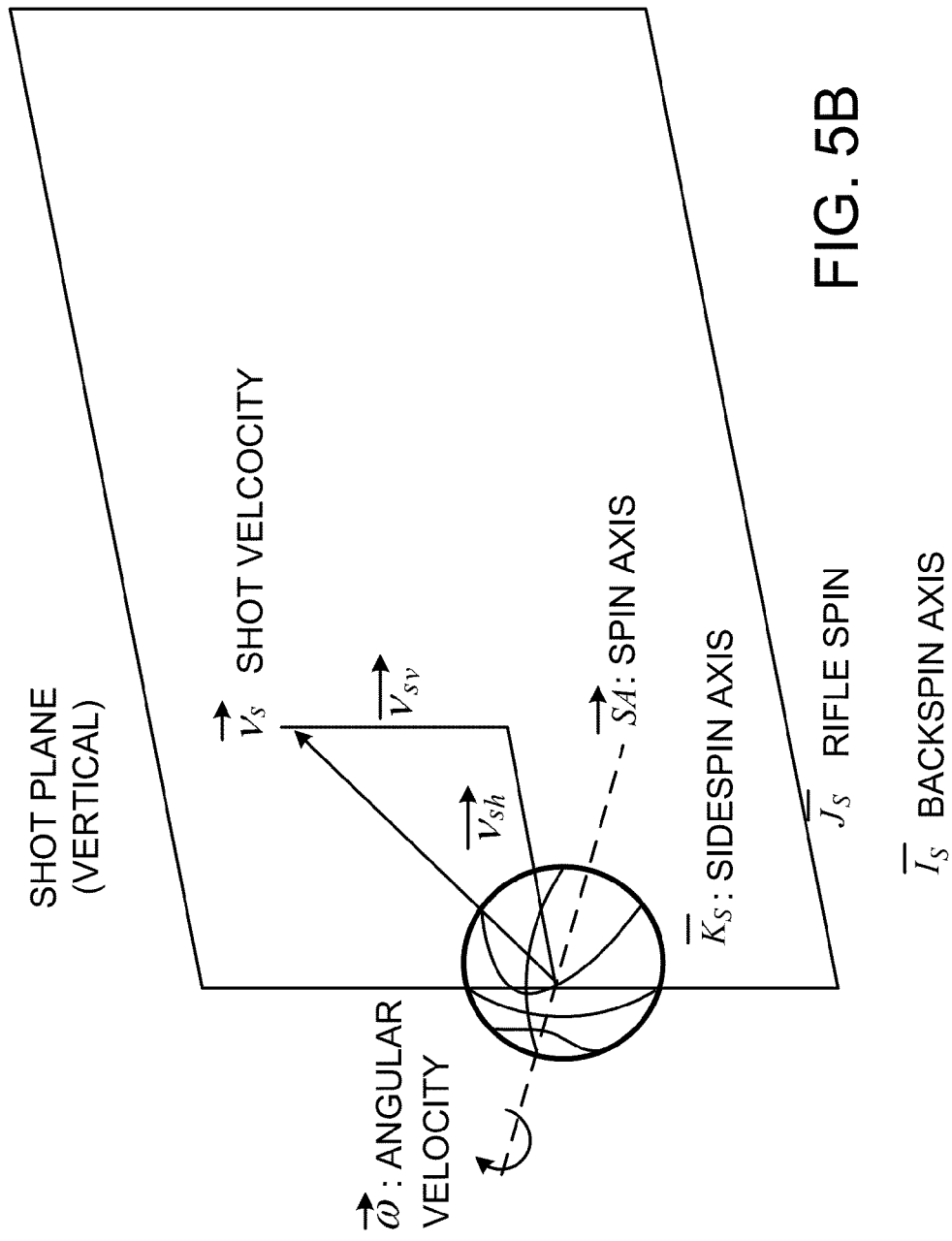

FIGS. 5A and 5B show parameters that can define a basketball shot. There are two key planes, the plane of the floor and the shot plane. The floor plane can be described by directions such as the baseline, vertical, and a unit vector that points from the center of the baseline to the center of the court (perpendicular to the baseline). This plane serves as a reference for key aspects of the court. The shot plane is better described in FIG. 5B, but metrics such as shot arc and shot distance are best described in FIG. 5A. Shot distance is the horizontal distance from the release position to the hoop position.

In the shot plane of FIG. 5B, the plane is defined by two vectors, a vertical unit vector and the shot velocity at the instance of release. The ball cannot leave this plane during its flight towards the basket because no forces or torques act on the ball (ignoring presence of wind, or air drag). The shot velocity at release, $\vec{v}_s$, can be decomposed into a horizontal component, $\vec{v}_{s_h}$, and a vertical component, $\vec{v}_{s_v}$. The shot arc is calculated as, $$\alpha = \tan^{-1} \frac{v_{s_v}}{v_{s_h}}.$$

When the ball is released it has some angular velocity, $\vec{\omega}$, about some spin axis, $\vec{SA}$. This spin can be decomposed about the shot plane axes, $[\overline{I}_s, \overline{J}_s, \overline{K}_s]$. Only spin about $\overline{I}_s$ leads to backspin and therefore spin about the other axes represents spin errors, assuming pure backspin is ideal shot technique.

Figure 6:
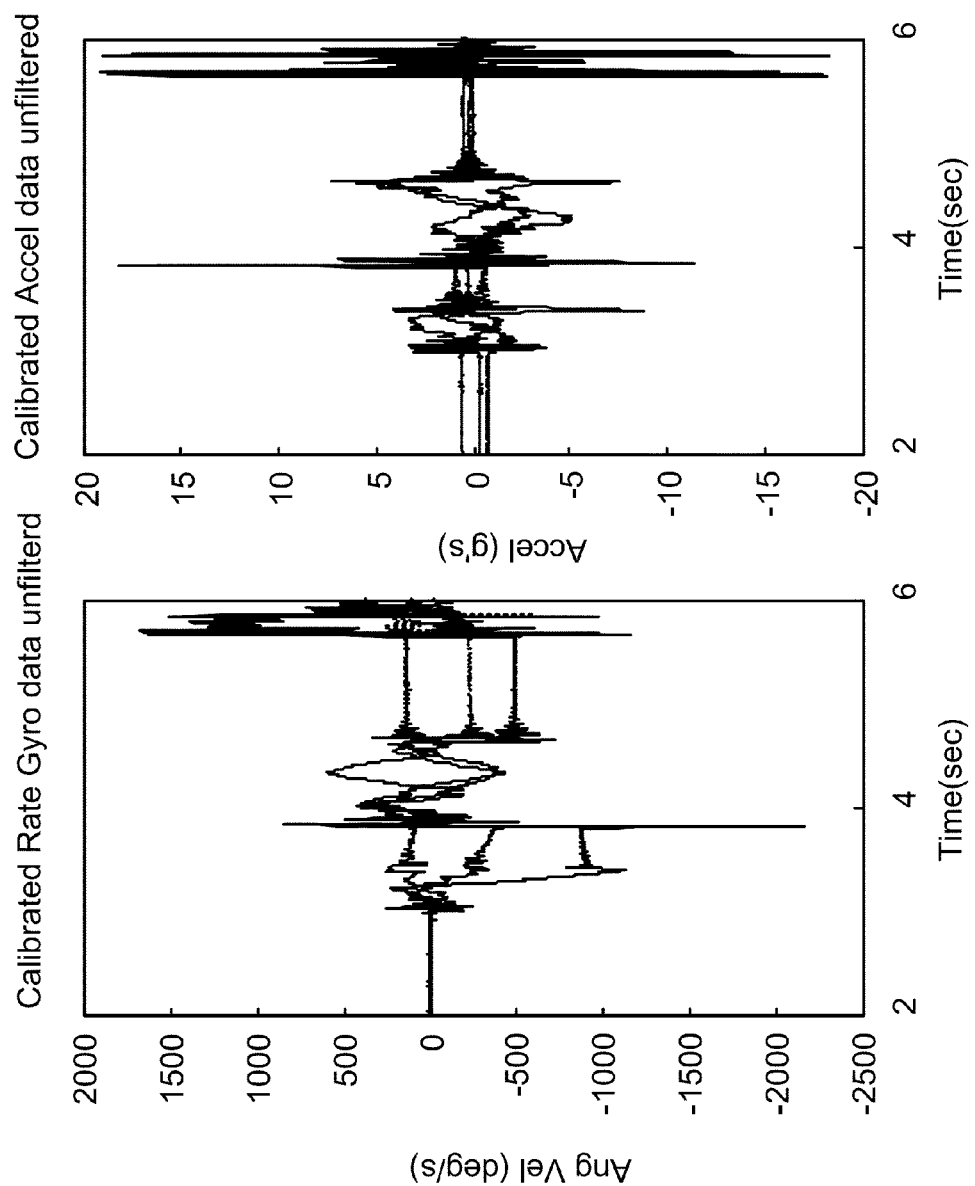
FIG. 6 shows example gyro and accelerometer data for a basketball shot.
Figure 7:
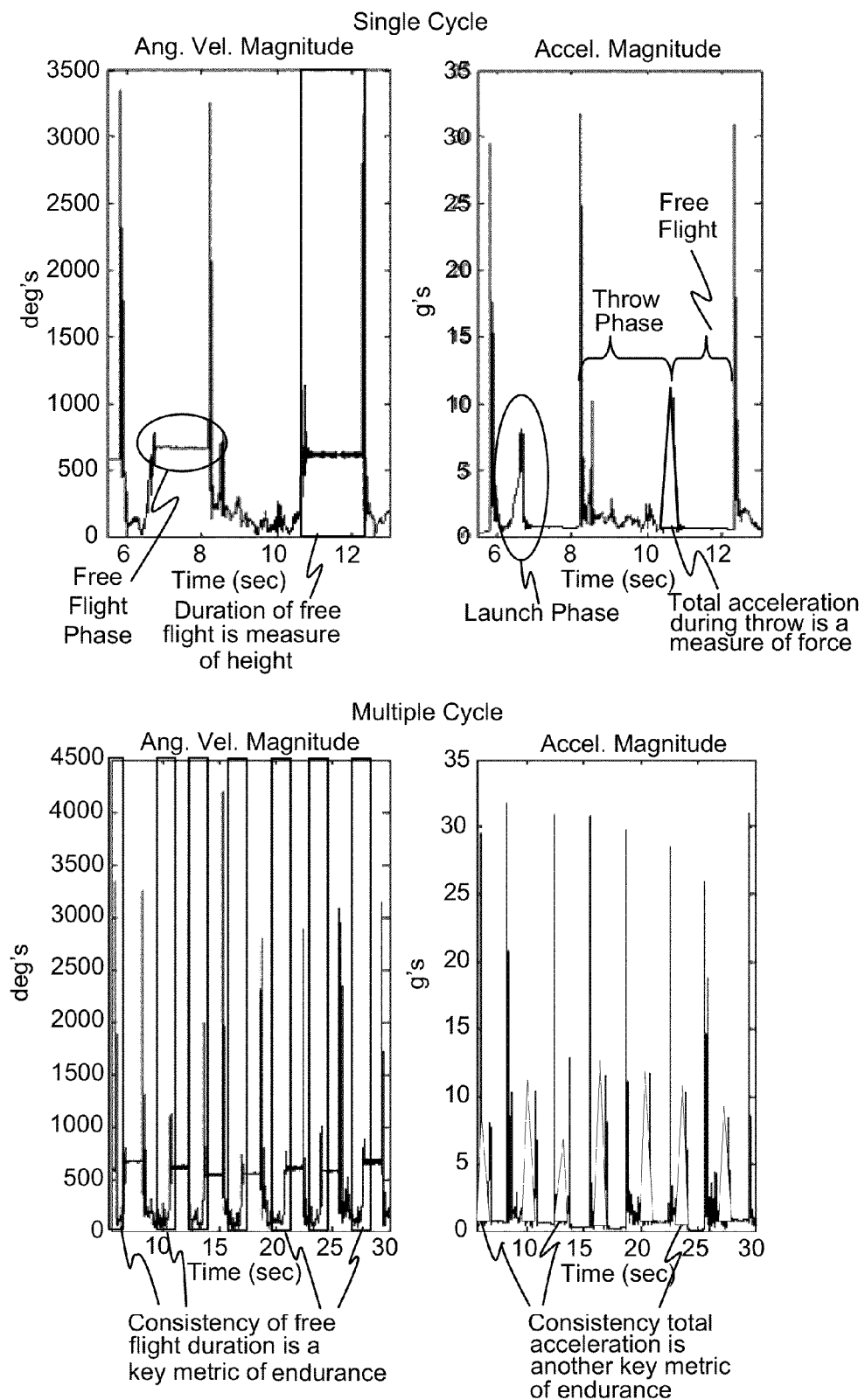
FIG. 7 shows example data from a ball being tossed upward from the chest of a lying subject.

FIG. 6 shows example gyro and accelerometer data for a basketball shot. The data is measured about a set of orthogonal body fixed axes. In order to calculate the shot plane and any metrics requiring the shot plane all six signals above along with some information about initial conditions are used.

Particular Description of Measured Exercises

This section describes particular artificial exercises that may be administered to an athlete, or human subject, so as to test features of the subject such as speed, quickness, strength, and stamina. The exercises are referred to as being artificial because they do not involve the subject actually performing actions that may occur in a game. Instead, they attempt to stress muscles or muscle groups that may be used in a game, and isolate the muscle groups so as to better localize a subject's strengths and weaknesses.

The exercises may be used to evaluate core strength and athletic ability using an instrumented ball, such as a basketball or medicine ball (ball with a specified weight so as to increase the force required to accelerate the ball.) Four example drills are described here to demonstrate different aspects of athleticism and strength that can be measured. The four drills are not meant to be an exhaustive list of the capabilities, but are instead intended to provide initial concepts for how an instrumented, weighted ball can be applied to athleticism and core strength measurement.

Drill 1: Vertical Chest Past from a Lying Down Position

Description: The subject lies on their back with the ball starting from rest on their chest. The subject then tries to throws the ball into the air using a chest pass form. The goal is to throw the ball as high as possible with maximum accuracy so that the ball returns to the subject's hands. This cycle can then be repeated for a number of throws or for a set amount of seconds.

Measurement Goals:

Height of the throw—measure the initial launch velocity and the time the ball is in the air and then calculate the height of the throw.

Force of the throw—measure the acceleration applied to the ball during the throw for a ball with known mass. Knowing the mass of the ball and the acceleration applied to it the force of the throw can be calculated.

Accuracy of throw—measure the initial velocity vector relative to the initial starting orientation to determine whether the ball is thrown straight up.

Consistency of Metric—For each metric above the variation across multiple throws can be used to determine consistency as an additional measure of proficiency.

Drill 2: Repeated Vertical Jump

Description: The subject holds the ball above their head and repeatedly tries to jump as high as possible. The subject is allowed to move the ball relative to directly above their head but sometime during each jump the ball should be fully extended above their head.

Measurement Goals

Height of jump—measure the initial velocity of the jump and the time of the jump to determine the height of the jump.

Speed of jump—measure the time the subject is on the ground as they load up to jump. This is important because 2 subjects may be able to obtain the same height of jump, but if 1 subject can generate the force required to jump to the height faster than the other, the faster subject has an advantage in the sport of basketball.

Consistency of Jump—by looking over a number of consecutive jumps the degradation of the above metrics is an indicator of ability and strength Drill 3: Sit-Up with Side Twists Description: The subject does a set of sit-ups or ties to do as many reps as possible during a defined number of seconds. A single rep starts from a laying down position with the ball held still, the subject then raises their shoulders off the ground to contract the abdominal muscles. While holding their shoulders off the ground the subject tries to move the ball side to side as fast as possible, in a twisting motion. Each twist is concluded by tapping the ball against the ground. During each rep there should be '2n' total twists, 'n' to the right and 'n' to the left.

Measurement Goals

Total number of reps—a measure of core strength is simply the number of reps the subject can complete in the allotted time Speed of taps/twists—as the subject completes a tap the time between taps can be measured and be used as a measure of core strength Consistency of rep time—as the subject completes multiple reps, both the single rep time and the consistency of rep time are important metrics of core strength. The consistency of rep time is an indication of core strength endurance.

Consistency of taps/twists—as the subject completes multiple reps and therefore multiple taps per rep, the consistency of the speed of taps is an indication of core strength endurance.

Drill 4: Chest Pass and Following Sprint

Description: The subject starts at Position 1 and the ball will initially be placed in a fixed stand. A second position, Position 2, is located a distance D from Position 1. The subject picks the ball up and throws a chest pass as far as possible. The distance D should be chosen so that it is unlikely the subject will be able to throw the ball past Position 2. A drill assistant waits near Position 2. Once the ball hits the ground after the chest pass the assistant grabs the ball and places it in a stand at Position 2. As soon as the subject throws the ball from Position 1 they sprint after it. The ball will be at the stand at position 2 before the subject arrives. As the subject arrives at Position 2 the subject picks up the ball, turns around and throws the ball back to Position 1, again as hard as possible, with a chest pass motion. A second drill assistant is waiting at Position 1 and as soon as the ball hits the ground the assistant grabs the ball and places it on the stand at Position 1. Then, as before, the subject sprints after the ball towards position 1 immediately after throwing the ball. This back and forth process is repeated as many times as possible during the allotted time.

Measurement Goals:

Distance of throw: by measuring the initial horizontal velocity of the ball and the time the ball is in the air the horizontal distance traveled can be calculated.

Force of throw: by measuring the acceleration of the ball during the throw phase along with knowing the mass of the ball the force of the throw can be calculated.

Sprint speed: the time from when the ball is thrown into the air up until the ball is picked up from the stand is a measure of how quick the subject has sprinted after the ball.

Consistency of metrics: this drill is designed to illuminate how a subject can perform a core strength task, throwing the ball, while under cardiovascular stress, sprinting. Therefore the consistency of distance of throw and force of throw are the main performance metrics of this drill.

Collection and Storage of Motion Data

This section describes an example system and process that permits the collection at a central system (e.g., a group of connected servers at a single physical site) of motion data from remote terminals, such as laptop computers that have been taken to physical rehabilitation facilities, sports fairs, and the like. The systems and processes permit motion data to be collected remotely and then passed to the server system for analysis and generation of human-understandable reporting from the data. Such a system may permit an organization to place a smaller amount of computing resources on mobile units, as compared to the central system. As a result, it may be easier to update analysis software because the updates do not need to be communicated to all of the various remote data collection units. Also, where a system is constantly gathering new data that it compares against test data as it arrives, a centralized system may have the benefit of providing a single place in which important data will be stored and analyzed. Also, an organization may keep better security over proprietary processes by running those processes on a secured server system, rather than scattering such information to a number of different users.

The system involves a software program connected to communication devices that confirms that motion data collected from a pre-defined series of athletic motion events has been collected into a repository, sent to a second repository, and then successfully processed by secondary algorithms prior to the completion of a physical activity event. The process involves collecting live motion data from sensors about a specific drill, storing and compressing a file locally, and automatically sending that compressed file to a second server where a program watches for its arrival. The program looks for a code at the end of the file to signal that the complete file has been received, before it is uploaded into a second processor and decompressed. The second server then sends it into a software process that counts the raw motion data and then computes a result. The result is sent back to the local machine. Along each of these touch points we confirm that files have been received and processed.

The system and process may also be described with respect to the following exemplary features:

A Process to ensure that real-time motion data is being collected from a specific player and a specific pre-determined series of motions that will result in a score.

A process to send large files to a central location for centralized data processing and storage, where a specific quantified result is returned to the sending location.

A system that delivers a scoring result within a specified time based on real-world motion data collected from a sports object. Ie—we know how to get a score back within 240 seconds after the completion of a motion event.

A system that creates personalized diagnostic reporting of a motion event based on the pre-defined motion movements (ie a sports drill) of a person. "Personalized" includes a summary of measurements, a comparison of measurements, and improvement strategies based on that score.

The following describes the process flow in more detail.

Step 1: Create Event and Assign Drill Package

CRM software allows a user to create an event and assign a package of drills to that event. Players that are registered for that event will work through the assigned drills. Once the event is created, the information is stored in the central database.

Step 2: Register a Player into the CRM System

A user may first input key demographic information: first and last name, DOB, sex, height, level of play, and email address. Once a player is registered, the information is stored in the central database and then that user can be registered for the event and drill package.

Step 3: Administer the Test to the Player

The process may then involve synchronizing an instrumented basketball with a data collection computer. This is done through a local database and a key parameters file. The individual drill test files associated with the event drill package are then collected. Each file name encodes the player's ID, the ID of the event at which the drill is being collected, the ID of the drill being completed, and the number of times that player has attempted the particular drill at the particular event. This same information along with the instrumented ball ID and player's height is encoded in the first line of the file. The file is initially created on the local machine. Other locations for encoding such information may also be used.

Once data collection is finished, the file is compressed and a CRC checksum of the compressed file is calculated and added to the file header. The file is then transferred to the central server via FTP. When the compressed file arrives and is acknowledged by a directory watchdog, the server calculates the CRC checksum of the file and compares it to the calculated value that is contained within the file header. If the CRC checksums match, then the file upload is declared complete and a decompression routine is triggered. The file output from decompression is sent to another directory which is being watched. When the decompression finishes, the file is handed to MatLab for data processing and a copy is placed in the archive directory.

MatLab starts by running a processing algorithm that determines when the drill is being executed and when the player has lost control. During the time when the player is controlling the ball, MatLab analyzes when the ball in contact with the players hand and when it is not. During the time when the ball is in contact, MatLab analyzes metrics about how the ball is being controlled (i.e. spin rate, force, etc.). MatLab finishes by exporting an analysis metrics file (if an error occurs an exception file is produced).

The output directories of MatLab (Export and Exception) are watched by another application. If a file appears in Exception, a notification of the failed test is sent out. If a file appears in Export, an attempt is made to import it into the database. If the record is a new record, then the file is imported into the database and a copy of the file is put into the archives. If the record already exists, the import is cancelled and the failed import is logged.

Once the file is imported into the database, the scoring algorithm runs. First, a check is made to see if the new database insert contains a top score for any of the scoring elements. If it does, the top metric scores are updated and the score is calculated. If it does not, then the score is calculated based on the previous top scores. The calculated score is then sent back to the remote computer as verification that data processing was completed. On the final drill of the sequence, the uploaded file contains additional encoded information to trigger generation of a total score and to send a report for that player to the event printer. At this point, the operator administering the test can see that the drills have been completed and scored. The score that is computed may be either absolute, according to a defined base line, or relative, as defined above a fixed or rolling (e.g., substantially constantly updated) score for a population of other players, including other players whose abilities have been benchmarked so that they may serve as a base point for determining skills of other players.

The report is generated on the server and archived so it can easily be retrieved either by the player though a website generated by the system or an operator through the CRM software.

Step 4: Making the Testing Results Accessible Through a Website

Each player is assigned a unique ID in the CRM database, which links the player to their test results. A player who has completed a test at any event can go to the website and login by providing their unique ID and their email address (the email address originally associated with their registration). With a valid login, the website queries the CRM database to determine which events the player attended and which reports are available. The player can select a report that they wish to view by selecting the event, the attempt, and what level of report they desire. There may or may not be a cost associated with retrieving this information based on if they pre-paid for some reports or if they select an advanced report. Once the transaction is completed, the report is automatically generated and emailed to the player.

Figure 12:
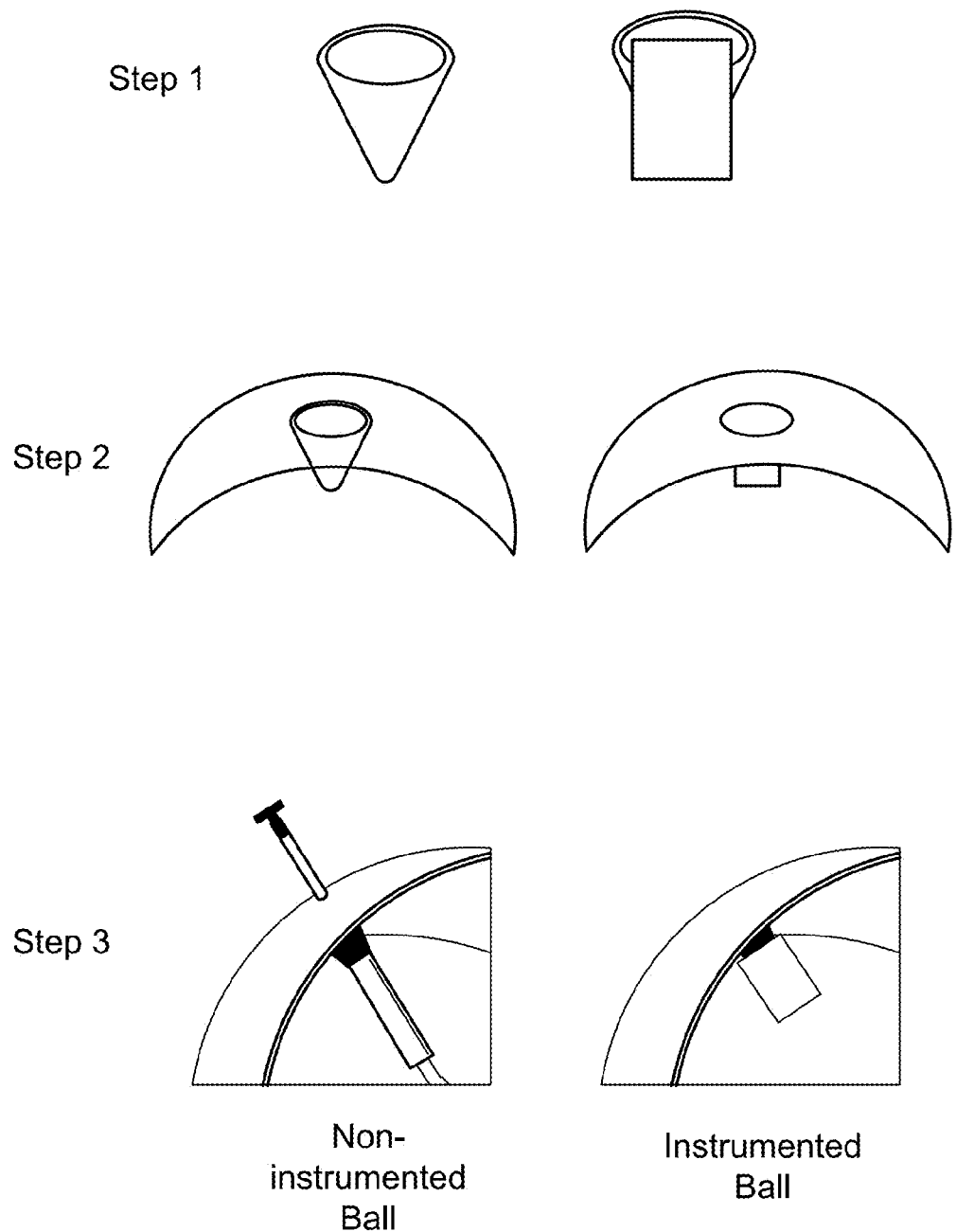
FIG. 12 shows a comparison between a process for making an non-instrumented basketball (or similar type of sporting ball) and an instrumented basketball.

FIG. 12 shows a comparison between a process for making a non-instrumented basketball (or similar type of sporting ball) and an instrumented basketball. In the figure, the non-instrumented manufacturing process is shown in the left-hand column, while the instrumented process is shown in the right-hand column. The three steps in each column show main actions that occur in the process, where the non-instrumented ball may be a Spalding Infusion pump ball. The Infusion basketball includes a built-in micro-pump that, with a twist, pops out of the ball and can be operated from outside the ball in order to inflate the ball. The pump may then be slid back into the ball and locked, and the ball may be used as normal.

In FIG. 12, the first step for both types of balls involves providing a rubber housing of an appropriate shape to be placed around the relevant hardware. The housing may include a peripheral edge along its upper end in a firm that is arranged to be fused with an inner bladder of a basketball. For example, the peripheral edge may define a generally circular shape that is substantially in a single plane, or in a slide convex plane that approximates the ultimate curve of a basketball.

The relevant hardware, such as a motion sensor may initially be assembled, programmed, and attached to a power source (battery), and may in certain implementations be encased in a flexible insulative material such as rubber that is attached to or is part of the housing. Although shown in the image as extending lengthwise into the ball, the sensor may be arranged in other manners so as to ensure that the sensor senses motion that reflects the actual motion of the ball, and also to ensure that the ball is balanced properly, and that such balance can be maintained across a large number of manufactured balls.

The encased sensor may then be fused to the inside surface of the inner bladder of the basketball and/or fused into a hole left for the sensor in the bladder. Such action may involve heating the rubber to its vulcanizing temperature and applying pressure to fuse the two rubber parts together. An appropriate temperature may be in the range of 90-170 degrees Celsius (194-338 degrees F.), though the temperature may be maintained below approximately 230 degrees Celsius, which may be the solder reflow temperature for manufacturing the sensor assembly. At this stage, the bladder may be made up of multiple separate panels that can then be attached to each other to form the shape of the ball.

In both processes, the ball may then be wound with a nylon thread to build up the inner carcass of the ball. The outer panels may then be molded onto the inner carcass, which part of the process may occur at about 90-170 degrees C. The molding temperature is a function of the rubber used in the basketball construction and that rubber's vulcanization temperature. Again, materials and temperatures may be selected to maintain the temperature of the sensor assembly below its solder reflow temperature. There may also be components that are part of the sensor assembly that require even lower temperatures.

In certain implementations, the sensor assembly may be inserted into the ball after it is manufactured via an aperture in the ball. In such a situation, the sensor could take the form of a long, narrow cylinder, and data transmission from the sensor assembly may occur either by removing the sensor assembly from the ball and physically attaching it to a computing device, by powered wireless transmission, or by passive wireless transmission. For example, a coil used for charging the sensor assembly may also be used to pass data across short distances (e.g., across the ball's wall) when it is interrogated by a corresponding loop in a reader on the outside of the ball. For example, if a base in which the ball is placed takes the form of a ring, the ring may have an electrical coil circling its periphery and the ball may be arranged so that a coil inside the ball is placed relative to the coil so that the sensor assembly can be both powered and interrogated. In certain implementations, a battery for the sensor assembly may also be inserted into the ball through a port, or aperture.

With the sensor assembly and its corresponding battery sealed inside the ball, access to the battery becomes a problem. Such a problem may be addresses by providing an inductive charging coil and related circuitry. As such, when the ball is placed into a recharging zone (which may be defined by a ball stand that includes a ring whose inner diameter is smaller than the outer diameter of the ball, and the coils are positioned to receive maximum charge when the ball is placed right-side up into the stand. Alternatively, or in addition, a recharging jack in the form of a female connector may be attached to the sensor assembly, and may be aligned with a hole in the exterior surface of the ball, much like a hole used by an air pump needle. A user may then insert a recharging jack into the hole in order to recharge the battery for the sensor assembly.

The sensor assembly may be activated and deactivated in various manners. As one example, the sensor assembly may be active all the time, and may simply operate until it runs down. In such a situation, an owner of a basketball would need to determine when he or she was going to conduct tests with the ball and then pre-charge it for an adequate time period. Alternatively, the ball may be programmed to enter a sleep mode when it is inactive for a set period of time (e.g., 10 minutes) and may be activated on such a timer when a motion sensor determines that the ball has been bounced or has been moved in a predetermined manner. Alternatively, a mechanical switch may be provided, such as through a port on the ball into which a pin or similar instrument may be inserted to turn the ball on or off. To confirm the user's input, the sensor assembly may provide a tone in response to the ball being turned on or off (e.g., rising tones for turning on, and falling tones for turning off).

Figure 14:
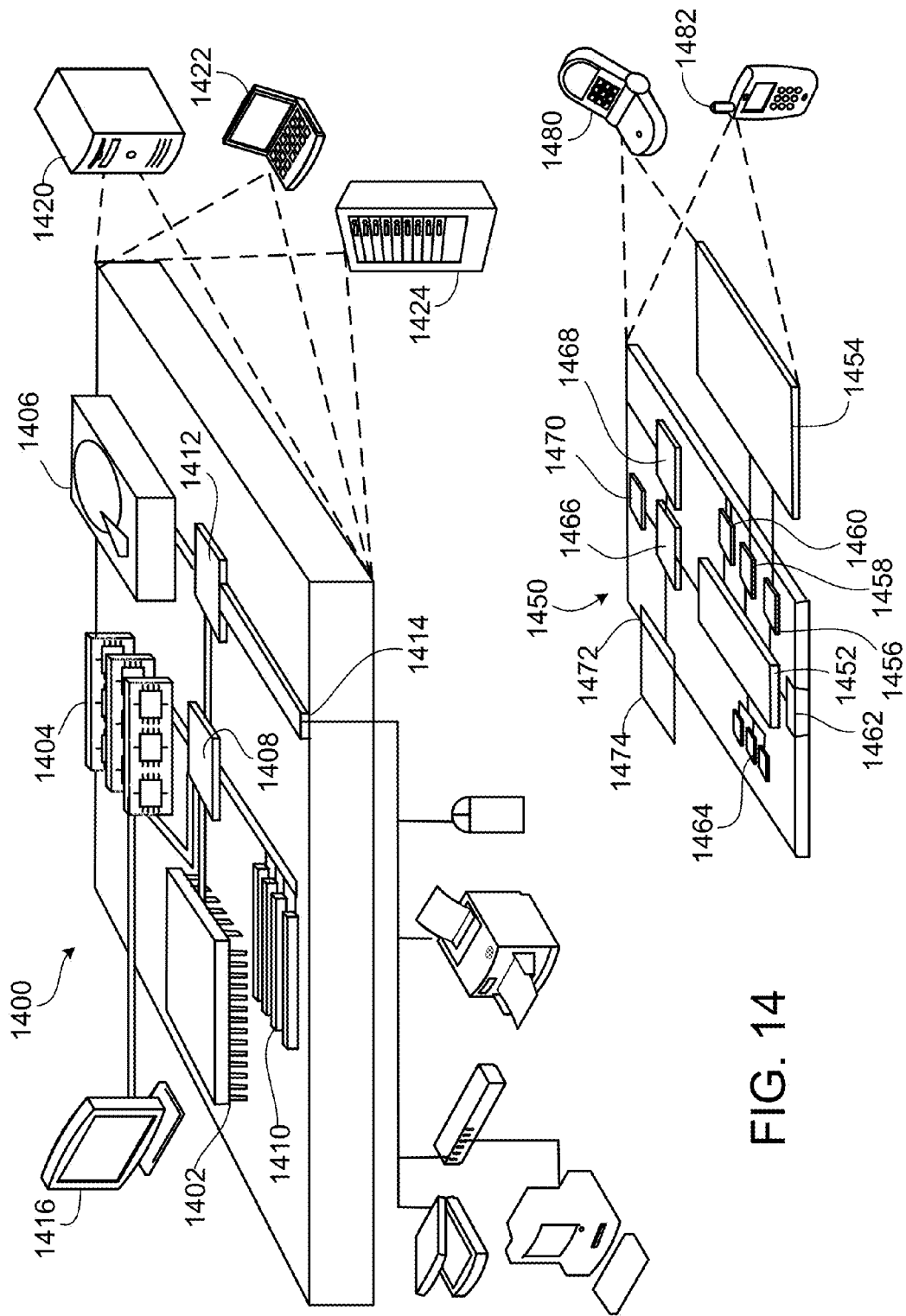
FIG. 14 shows an example of a computer device and a mobile computer device that can be used to implement the techniques described here.

FIG. 14 shows an example of a generic computer device 1400 and a generic mobile computer device 1450, which may be used with the techniques described here. Computing device 1400 is intended to represent various forms of digital computers, such as laptops, desktops, workstations, personal digital assistants, servers, blade servers, mainframes, and other appropriate computers. Computing device 1450 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the inventions described and/or claimed in this document.

Computing device 1400 includes a processor 1402, memory 1404, a storage device 1406, a high-speed interface 1408 connecting to memory 1404 and high-speed expansion ports 1410, and a low speed interface 1415 connecting to low speed bus 1414 and storage device 1406. Each of the components 1402, 1404, 1406, 1408, 1410, and 1415, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as display 1416 coupled to high speed interface 1408. In other implementations, multiple processors and/or multiple buses may be used, as appropriate, along with multiple memories and types of memory. Also, multiple computing devices 1400 may be connected, with each device providing portions of the necessary operations (e.g., as a server bank, a group of blade servers, or a multi-processor system).

The memory 1404 stores information within the computing device 1400. In one implementation, the memory 1404 is a volatile memory unit or units. In another implementation, the memory 1404 is a non-volatile memory unit or units. The memory 1404 may also be another form of computer-readable medium, such as a magnetic or optical disk.

The storage device 1406 is capable of providing mass storage for the computing device 1400. In one implementation, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 1404, the storage device 1406, memory on processor 1402, or a propagated signal.

The high speed controller 1408 manages bandwidth-intensive operations for the computing device 1400, while the low speed controller 1415 manages lower bandwidth-intensive operations. Such allocation of functions is exemplary only. In one implementation, the high-speed controller 1408 is coupled to memory 1404, display 1416 (e.g., through a graphics processor or accelerator), and to high-speed expansion ports 1410, which may accept various expansion cards (not shown). In the implementation, low-speed controller 1415 is coupled to storage device 1406 and low-speed expansion port 1414. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1400 may be implemented in a number of different forms, as shown in the figure. For example, it may be implemented as a standard server 1420, or multiple times in a group of such servers. It may also be implemented as part of a rack server system 1424. In addition, it may be implemented in a personal computer such as a laptop computer 1422. Alternatively, components from computing device 1400 may be combined with other components in a mobile device (not shown), such as device 1450. Each of such devices may contain one or more of computing device 1400, 1450, and an entire system may be made up of multiple computing devices 1400, 1450 communicating with each other.

Computing device 1450 includes a processor 1452, memory 1464, an input/output device such as a display 1454, a communication interface 1466, and a transceiver 1468, among other components. The device 1450 may also be provided with a storage device, such as a microdrive or other device, to provide additional storage. Each of the components 1450, 1452, 1464, 1454, 1466, and 1468, are interconnected using various buses, and several of the components may be mounted on a common motherboard or in other manners as appropriate.

The processor 1452 can execute instructions within the computing device 1450, including instructions stored in the memory 1464. The processor may be implemented as a chipset of chips that include separate and multiple analog and digital processors. The processor may provide, for example, for coordination of the other components of the device 1450, such as control of user interfaces, applications run by device 1450, and wireless communication by device 1450.

Processor 1452 may communicate with a user through control interface 1458 and display interface 1456 coupled to a display 1454. The display 1454 may be, for example, a TFT LCD (Thin-Film-Transistor Liquid Crystal Display) or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452.

In addition, an external interface 1462 may be provide in communication with processor 1452, so as to enable near area communication of device 1450 with other devices. External interface 1462 may provide, for example, for wired communication in some implementations, or for wireless communication in other implementations, and multiple interfaces may also be used.

The memory 1464 stores information within the computing device 1450. The memory 1464 can be implemented as one or more of a computer-readable medium or media, a volatile memory unit or units, or a non-volatile memory unit or units. Expansion memory 1474 may also be provided and connected to device 1450 through expansion interface 1472, which may include, for example, a SIMM (Single In Line Memory Module) card interface. Such expansion memory 1474 may provide extra storage space for device 1450, or may also store applications or other information for device 1450. Specifically, expansion memory 1474 may include instructions to carry out or supplement the processes described above, and may include secure information also. Thus, for example, expansion memory 1474 may be provide as a security module for device 1450, and may be programmed with instructions that permit secure use of device 1450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1464, expansion memory 1474, memory on processor 1452, or a propagated signal that may be received, for example, over transceiver 1468 or external interface 1462.

Device 1450 may communicate wirelessly through communication interface 1466, which may include digital signal processing circuitry where necessary. Communication interface 1466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1468. In addition, short-range communication may occur, such as using a Bluetooth, WiFi, or other such transceiver (not shown). In addition, GPS (Global Positioning System) receiver module 1470 may provide additional navigation- and location-related wireless data to device 1450, which may be used as appropriate by applications running on device 1450.

Device 1450 may also communicate audibly using audio codec 1460, which may receive spoken information from a user and convert it to usable digital information. Audio codec 1460 may likewise generate audible sound for a user, such as through a speaker, e.g., in a handset of device 1450. Such sound may include sound from voice telephone calls, may include recorded sound (e.g., voice messages, music files, etc.) and may also include sound generated by applications operating on device 1450.

The computing device 1450 may be implemented in a number of different forms, as shown in the figure. For example, it may be implemented as a cellular telephone 1480. It may also be implemented as part of a smartphone 1482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention. For example, much of this document has been described with respect to measuring motion data for particular drills, though other forms of data gathering and comparison may also be employed.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

The invention claimed is:

1. A computer-implemented athletic performance analysis method, comprising:
   generating, by one or more electronic sensors coupled within a physical basketball, motion data that characterizes motion of the basketball resulting from a human player handling the basketball, wherein the motion comprises impacts from bounces of the physical basketball;
   obtaining, by a processor coupled within the basketball, the motion data;
   processing, by the processor, the motion data to produce processed data that reflects athletic performance corresponding to the human player handling the basketball; and
   transmitting, by a wireless transmitter coupled within the basketball, the processed data;
   receiving, by a smart phone, the processed data transmitted from the wireless transmitter;
   graphically representing, on a display of the smart phone, the processed data;
   entering a sleep mode after the physical basketball has been inactive for a period of time; and
   activating the physical basketball from the sleep mode in response to detection that the physical basketball has been moved in a predetermined manner.

2. The method of claim 1, wherein the one or more electronic sensors comprise (a) one or more accelerometers or (b) one or more angular rate gyroscopes.

3. The method of claim 1, wherein the motion comprises shooting the physical basketball.

4. The method of claim 1, wherein the motion comprises spin of the physical basketball.

5. The method of claim 1, wherein the motion comprises acceleration of the physical basketball.

6. The method of claim 1, wherein the transmitting comprises using BLUETOOTH communications.

7. The method of claim 1, wherein processing the motion data comprises scoring the motion data.

8. The method of claim 1, wherein processing the motion data comprises analyzing patterns of forces on the physical basketball over time.

9. The method of claim 1, wherein the processed data characterizes motion of the physical basketball that was obtained at multiple separate occasions.

10. The method of claim 1, wherein the graphic representation comprises an indicator of performance that involves a value displayed along a predetermined scale.

11. The method of claim 1, wherein one or more batteries are coupled within the physical basketball and electrically coupled to the one or more electronic sensors.

12. The method of claim 11, further comprising inductively charging the one or more batteries.

13. A athletic performance analysis system comprising:
   one or more processors configured to execute computer program instructions; and
   computer storage media encoded with computer program instructions that, when executed by one or more processors, cause a computer device to perform operations comprising:
   generating, by one or more electronic sensors coupled within a physical basketball, motion data that characterizes motion of the basketball resulting from a human player handling the basketball, wherein the motion comprises impacts from bounces of the physical basketball;
   obtaining, by at least one processors coupled within the basketball, the motion data;
   processing, by at least one of the processors coupled within the basketball, the motion data to produce processed data that reflects athletic performance corresponding to the human player handling the basketball;
   transmitting, by a wireless transmitter coupled within the basketball, the processed data;
   receiving, by a smart phone, the processed data transmitted from the wireless transmitter;
   graphically representing, on a display of the smart phone, the processed data;
   entering a sleep mode after the physical basketball has been inactive for a period of time; and
   activating the physical basketball from the sleep mode in response to detection that the physical basketball has been moved in a predetermined manner.

14. The system of claim 13, wherein the one or more electronic sensors comprise (a) one or more accelerometers or (b) one or more angular rate gyroscopes.

15. The system of claim 13, wherein the transmitting comprises using BLUETOOTH communications.

16. The system of claim 13, wherein processing the motion data comprises analyzing patterns of forces on the physical basketball over time.

17. The system of claim 13, wherein the processed data characterizes motion of the physical basketball that was obtained at multiple separate occasions.

18. The system of claim 13, wherein the graphic representation comprises an indicator of performance that involves a value displayed along a predetermined scale.

19. The system of claim 13, wherein one or more batteries are coupled within the physical basketball and electrically coupled to the one or more electronic sensors.

20. The system of claim 19, further comprising inductively charging the one or more batteries.

* * * * *